(12) United States Patent
Ho et al.

(10) Patent No.: US 8,997,744 B2
(45) Date of Patent: Apr. 7, 2015

(54) ADJUSTABLE CONDUIT COUPLING ASSEMBLY

(75) Inventors: Peter Chi Fai Ho, Pittsburgh, PA (US); Jerome Matula, Apollo, PA (US); Lance Busch, Trafford, PA (US)

(73) Assignee: RIC Investments, LLC, Wilmington, DE (US)

( * ) Notice: Subject to any disclaimer, the term of this patent is extended or adjusted under 35 U.S.C. 154(b) by 193 days.

(21) Appl. No.: 13/083,892

(22) Filed: Apr. 11, 2011

(65) Prior Publication Data

US 2011/0180070 A1 Jul. 28, 2011

Related U.S. Application Data

(63) Continuation of application No. 11/653,708, filed on Jan. 16, 2007, now Pat. No. 7,931,026.

(60) Provisional application No. 60/760,793, filed on Jan. 20, 2006.

(51) Int. Cl.
| | |
|---|---|
| *A62B 18/02* | (2006.01) |
| *A62B 18/08* | (2006.01) |
| *A61M 16/06* | (2006.01) |
| *A61M 16/08* | (2006.01) |

(52) U.S. Cl.
CPC .............. *A61M 16/08* (2013.01); *A61M 16/06* (2013.01); *A61M 16/0638* (2013.01); *A61M 16/0816* (2013.01)

(58) Field of Classification Search
CPC ............ A61M 16/06; A61M 16/0666; A61M 16/0683; A61M 2016/0633; A61M 2016/0638; A61M 2016/0644; A61M 2016/065; A61M 2016/0655; A62B 18/02; A62B 18/025; A62B 18/06
USPC ............ 128/205.25, 206.21, 206.23, 206.24, 128/206.27, 206.28, 207.11, 207.13
See application file for complete search history.

(56) References Cited

U.S. PATENT DOCUMENTS

| | | | | |
|---|---|---|---|---|
| 4,287,613 | A | 9/1981 | Schulz | |
| 6,427,694 | B1 * | 8/2002 | Hecker et al. | 128/206.21 |
| 6,494,207 | B1 | 12/2002 | Kwok | |
| 6,516,802 | B2 | 2/2003 | Hansen | |
| 6,520,182 | B1 | 2/2003 | Gunarathnam | |
| 6,595,214 | B1 | 7/2003 | Hecker | |
| 6,615,834 | B2 | 9/2003 | Gradon | |
| 6,823,869 | B2 * | 11/2004 | Raje et al. | 128/206.24 |
| 7,357,136 | B2 | 4/2008 | Ho | |
| 7,931,026 | B2 * | 4/2011 | Ho et al. | 128/207.11 |
| 2001/0015204 | A1 * | 8/2001 | Hansen et al. | 128/205.25 |
| 2002/0096176 | A1 * | 7/2002 | Gunaratnam et al. | 128/207.11 |
| 2002/0148473 | A1 * | 10/2002 | Kwok et al. | 128/207.11 |
| 2003/0000533 | A1 | 1/2003 | Olsen | |
| 2003/0208146 | A1 | 11/2003 | Kania | |
| 2004/0216747 | A1 | 11/2004 | Jones | |
| 2005/0076913 | A1 * | 4/2005 | Ho et al. | 128/206.27 |
| 2005/0081858 | A1 | 4/2005 | Raje | |

(Continued)

*Primary Examiner* — Valerie L Skorupa
(74) *Attorney, Agent, or Firm* — Michael W. Haas

(57) ABSTRACT

A conduit coupling assembly for use in connection with a patient interface device. The conduit coupling assembly includes a coupling retention assembly for retaining the conduit coupling in a predetermined position with respect to the user's face, and an adjustment assembly that permits continuous adjustment of a position of the conduit coupling with respect to a user's face. The conduit coupling assembly is continuously adjustable and retainable in an adjusted position and orientation by the adjustment assembly.

21 Claims, 33 Drawing Sheets

(56) References Cited

U.S. PATENT DOCUMENTS

| | | | |
|---|---|---|---|
| 2005/0150499 A1* | 7/2005 | Bordewick et al. ...... 128/206.27 |
| 2006/0011202 A1 | 1/2006 | Kwok | |
| 2006/0185675 A1* | 8/2006 | Colin ...................... 128/206.24 |
| 2006/0213521 A1* | 9/2006 | Radney ................... 128/207.11 |
| 2006/0283452 A1 | 12/2006 | Woodard | |
| 2006/0283460 A1* | 12/2006 | Brown et al. ............ 128/206.24 |

\* cited by examiner

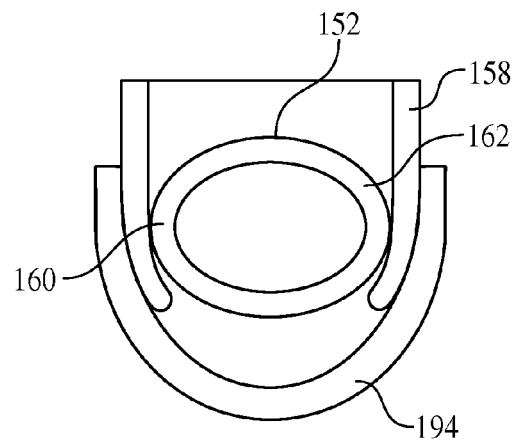 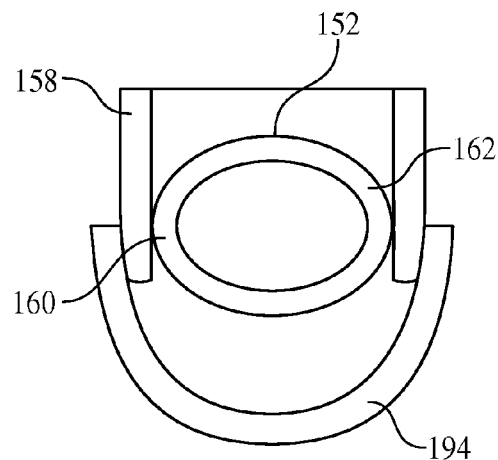
FIG. 38A  FIG. 38B
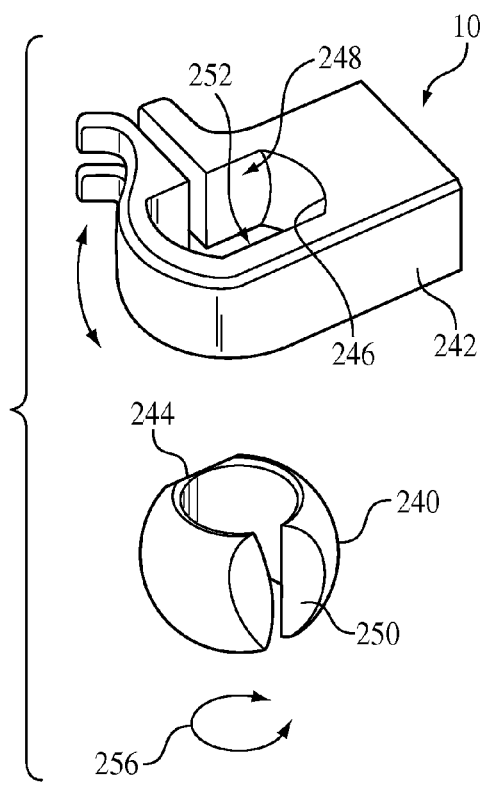 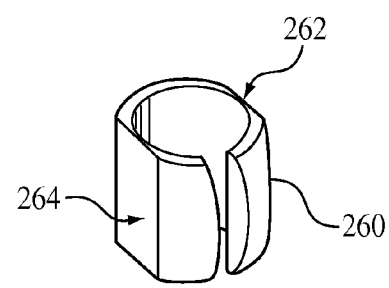
FIG. 39  FIG. 40

ADJUSTABLE CONDUIT COUPLING ASSEMBLY

CROSS-REFERENCE TO RELATED APPLICATIONS

This application is a Continuation under 35 U.S.C. §120 of U.S. patent application Ser. No. 11/653,708, filed Jan. 16, 2007, now U.S. Pat. No. 7,931,026, which claims priority under 35 U.S.C. §119(e) from provisional U.S. patent application No. 60/760,793, filed Jan. 20, 2006, the contents of which are incorporated herein by reference.

BACKGROUND OF THE INVENTION

1. Field of the Invention

The present invention relates generally to structures and assemblies for use in connection with a patient interface device, and, in particular, to an adjustable conduit coupling assembly for providing adjustability of the position and orientation of a conduit coupling that joins a patient interface device to a patient circuit.

2. Description of the Related Art

It is well known to diagnose, treat, or monitor the condition of the patient using a patient interface device that communicates with the airway of a patient. For example, a patient may be monitored and treated for various sleep disorders, such as obstructive sleep apnea (OSA), which is characterized by a collapse of at least a portion of the upper airway during sleep, central apneas, which are characterized by the suspension of all respiratory movement, or a combination of both OSA and central apneas, referred to as mixed apnea. Monitoring and treating these disorders typically involves providing a patient interface device, such as a nasal mask, nasal/oral mask, mouth mask, full-face mask, nasal cannula, nasal prongs, nasal pillows, etc., in communication with the airway of the user, such as the user's nose, mouth, or both, and delivering a pressure support therapy to the airway of the patient.

Examples of conventional pressure support devices that deliver a pressure support therapy include a continuous positive airway pressure (CPAP) device or a device that delivers a variable airway pressure. Examples of variable pressure support devices include a bi-level pressure support, which varies the pressure delivered with the patient's respiratory cycle, or a proportional positive airway pressure (PPAP) therapy, which varies the pressure based on the monitored flow (example of this include C-Flex and Bi-Flex). It is also know to vary the pressure delivered to the patient based on a monitored condition of the patient, such as whether the patient is experiences snoring, apneas, hypopneas, flow limitations, respiratory event related arousals (RERAs), upper airway resistance, etc., which is referred to as an auto-titration pressure support system, because the system attempts to control the pressure itself so as to deliver only the pressure needed to treat the medical disorder, such as sleep apnea syndrome, in particular, OSA, congestive heart failure, stroke, Cheynes-Stokes respiration, etc.

Further, there are numerous situations where it is necessary or desirable to deliver a flow of breathing gas non-invasively, to the airway of a patient, i.e., without intubating the patient or surgically inserting a tracheotomy tube in their trachea. For example, it is known to ventilate a patient using a technique known as non-invasive ventilation in lieu of invasive ventilation. Non-invasive ventilation and pressure support therapies involve the placement of a mask, which is typically a nasal or nasal/oral mask, on the face of patient to interface the ventilator with the airway of the patient. For purposes of the present invention, the phrase "pressure support system", "pressure support device," or "positive pressure support" includes any medical device or method that delivers a flow of breathing gas to the airway of a patient including non-invasive ventilation system.

Because patient interface devices are typically worn for an extended period of time, a variety of concerns must be taken into consideration. For example, in providing CPAP or other positive pressure therapy to treat OSA, the patient normally wears the mask all night long while he or she sleeps. One concern in such a situation is that the patient interface device is as comfortable as possible, otherwise the patient may avoid wearing the device, defeating the purpose of the prescribed pressure support therapy.

A typical mask type patient interface device includes a mask shell having a cushion attached to the shell that contacts the surface of the patient. The mask shell and cushion, which are referred to as the patient interface device, are held in place by a headgear assembly that wraps around the head of the patent. The patient interface device and headgear assembly form a patient interface assembly. A typical headgear assembly has flexible, adjustable straps that extend from the patient interface device to attach the mask to the patient. Other techniques for attaching a patient interface devices use a vice-like headgear that anchors at the front and back of the patient's head to support the mask on the user. See, e.g., U.S. Pat. No. 6,516,802. While such conventional patient interface devices are generally accepted, there remains a class of patients that do not find these devices to be sufficiently comfortable, too bulky, not providing a sufficient seal, or otherwise inadequate. Thus, alternative techniques for interfacing a pressure support system to the airway of a patient are desired.

In a conventional pressure support system, a flexible conduit is coupled to an outlet port of the pressure generating system. The flexible conduit is typically referred to as a "patient circuit" or "breathing circuit" and carries the flow of breathing gas from the pressure generating system to the patient interface device. In a typically arrangement, a patient interface device, such as a mask, is provided at the end of the patient circuit. A conduit coupling connects the patient circuit with the patient interface. In some arrangements, the conduit coupling is a permanent part of the mask, and, thus, forms part of the patient interface device. In other arrangements, the conduit coupling is considered part of the patient circuit. In either arrangement, the flow of gas is coupled to the airway of the patient by the patient interface device, so that the elevated pressure gas flow is delivered to the patient's airway.

Because patient interface assemblies are typically worn for an extended period of time, another concern is that the patient interface device provide a seal against the surface of the patient the is relatively fee of leaks or minimizes leaks. That is, the headgear must maintain the mask in a tight enough seal against a patient's face to be relatively leak free and do so without discomfort. Adjustability of the mask and/or the headgear, together with increased patient comfort, is also of importance. Similarly, when using a nasal mask, the conduit coupling, which couples the patient circuit to the mask (typically an rigid elbow), should be adjustable. This allows the patient to manipulate the angle, orientation, and/or position of the conduit coupling with respect to the user's face and/or forehead. As the patient engages in different activities, changes sleep positions, and over the course of time, for the sake of convenience and comfort, the conduit coupling should allow for maximum adjustability.

Various embodiments of mask assemblies are known that allow for the variable positioning of conduit couplings, and therefore the mask, as well as the conduit through which gas flows to the mask relative to the patient. For example, U.S. Pat. No. 6,823,869 discloses a mask assembly that provides for some limited adjustment of the conduit coupling with respect to the patient's face. However, the assembly of the '869 patent, while providing some adjustability of orientation and position of the conduit coupling, provides only limited adjustment options, such that the patient is not offered a limitlessly adjustable conduit coupling. A modified headgear or headgear assembly for use in positioning the patient interface and conduit coupling with respect to the patient's face is disclosed in U.S. Pat. Nos. 6,494,207 and 6,615,834.

Another conduit coupling assembly that is adjustable is disclosed in U.S. Pat. No. 6,595,214. In the '214 patent, a forehead-plate mount 9 is arranged between stops of a mask-holding part 2 and an intermediate hose 5 on an elongate tube 3. The forehead-plate mount 9 is integrally connected to a forehead plate 10, and straps are attached to the forehead plate 10 by eyelets 11 and 12. These straps are guided over the head in order for the nasal breathing mask to be held in place. The nasal breathing mask is positioned by pulling the entire unit over the head of the patient. The optimum distance between the forehead plate 10 and a mask part 1, which is a result of the anatomy of the user, i.e. of the distance between the forehead and the nose, is set by an axial adjustment of the forehead-plate mount 9 on the elongate tube 3. This axial setting is effected by means of a clamping connection between elongate tube 3 and forehead-plate mount 9. The forehead-plate mount 9 extends is a U-shaped collar 24, which is open toward the front. The inner surface of the collar has recesses 13 extending parallel to one another in the axial direction and annularly in the circumferential direction, at regular intervals. Mating annular ribs 14 are formed on the circumferential surface of the elongate tube and can be releasably inserted into these recesses 13. Accordingly, the forehead-plate mount 9 allows for the lateral adjustment of the conduit or tube.

SUMMARY OF THE INVENTION

Accordingly, it is an object of the present invention to provide a conduit coupling assembly that overcomes the shortcomings of conventional mask mounting assemblies. This object is achieved by providing an adjustable conduit coupling assembly that includes an adjustment assembly coupled to a conduit coupling and configured to permit continuous adjustment of a position of such a conduit coupling with respect to a user's face. In addition, a coupling retention assembly is provided. The coupling retention assembly is configured to retain the adjustment assembly in a predetermined position with respect to such a user's face. The conduit coupling is adjustable from a first position to a second position by the adjustment assembly over a continuous range of positions, and is retained or maintained in the second position by the adjustment assembly.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

BRIEF DESCRIPTION OF THE DRAWINGS

FIGS. 38A and 38B are a top views of the adjustable conduit coupling assembly of FIG. 37 shown in a locked position and an open position, respectively;

FIG. 39 is an exploded view of still another embodiment of an adjustable conduit coupling assembly according to the principles of the present invention; and FIG. 40 is a perspective view of an alternative configuration for the collar suitable for use in the conduit coupling assembly of the present invention.

DETAILED DESCRIPTION OF THE EXEMPLARY EMBODIMENTS

The present invention is directed to a conduit coupling assembly 10 as illustrated in various embodiments in FIGS. 1-37, which is used in a patient interface assembly that is worn a user's head, and in particular, on a user's face A and/or a user's forehead B, as shown, for example, in FIGS. 1, 6, 7, 10, 16, and 24-28. It is to be noted that directional phrases used herein, such as, for example, horizontal, vertical, left, right, clockwise, counterclockwise, top, bottom, up, down, front, rear, and derivatives thereof, relate to the orientation of the elements shown in the accompanying drawings and are not limiting upon the claims unless expressly recited therein.

Figure 1:
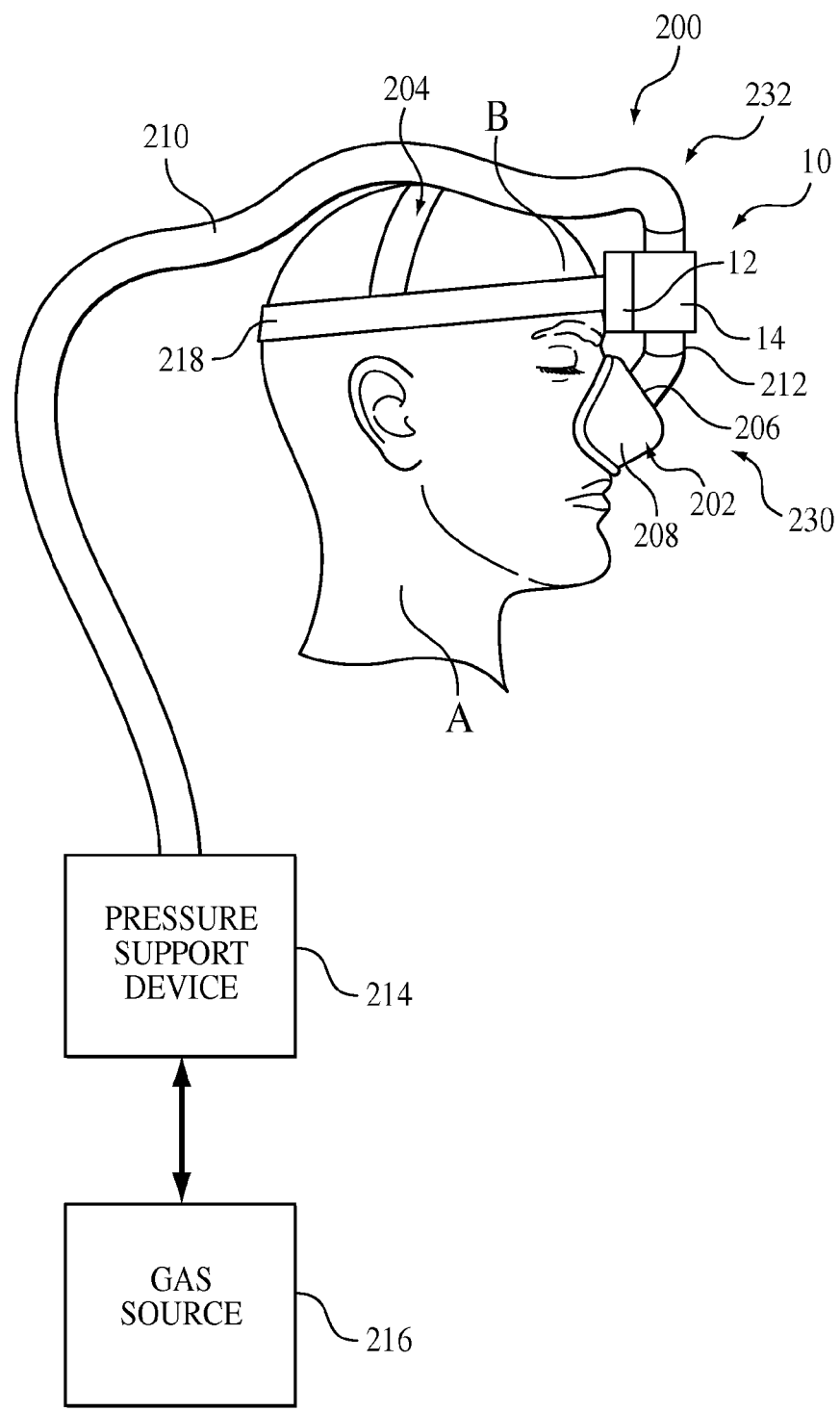
FIG. 1 is a schematic view of an adjustable conduit coupling assembly according to the principles of the present invention.

Referring now to FIG. 1, conduit coupling assembly 10 is designed to be used in connection with or as part of a patient interface system 200, which includes a patient interface device 202 and a headgear assembly 204. The present invention contemplates that patient interface device 202 is a nasal mask, a nasal/oral mask, a full-face mask, a nasal cannula, nasal pillows, an oral mouth piece, a tracheal tube, an endotracheal tube, similar patient interface devices 202 and structures as are known in the art that communicate with an airway of the patient.

Patient interface device 202 includes a port 206 extending through a wall 208 of the patient interface, which in this illustrated embodiment is a nasal mask. In this manner, port 206 allows gas, such as oxygen, air and the like, to flow through the port and into patient interface device 202 for inhalation by the patient. In order to provide gas to the patient, patient interface device 202 is in fluid communication with a patient circuit or conduit 210 via a conduit coupling 212. Conduit 210, in turn, is in fluid communication with a pressure support device 214 and/or a gas source 216. Specifically, gas flows from pressure support device 214 and/or the gas source 216 through conduit 210, further through a conduit coupling 212 and into patient interface device 202.

Normally, when using a variety of patient interface devices 202, such as a nasal mask, a nasal/oral mask, nasal pillows or prongs, and a nasal cannula, conduit coupling 212 extends from the patient interface device in a vertical direction up and adjacent the user's forehead B, where conduit 210 is attached to conduit coupling 212. In conventional systems, conduit 210 is retained by or attached to a headgear assembly 204 in order to prevent the conduit 210 from excessive motion. Because many patients are required to utilize patient interface device 202 for an extended period of time, the patient may desire to change the positioning of conduit coupling 212 with respect to the user's face A or user's forehead B. In addition, in order to provide one size or configuration for the patient interface device, it is necessary to provide adjustability of the conduit coupling relative to the user's face. For example, the patient may wish to angularly adjust or laterally adjust conduit coupling 212 to various positions with respect to his or her face A to provide a more comfortable fit. It is this type of adjustment that conduit coupling assembly 10 of the present invention provides.

In an exemplary embodiment of a headgear assembly 204 for use in the patient interface system of the present invention, the headgear assembly includes at least one, and typically multiple, straps 218 for retaining patient interface device 202 and/or conduit coupling 212 in a specified position with respect to the user's face A. In particular, headgear assembly 204 serves to hold patient interface device 202 in a sealed position on the user's face A. Still further, and as is known in the art, straps 218 can be adjustable with respect to patient interface device 202, conduit coupling 212 and other portions of patient interface system 200. This adjustability allow the user to control or adjust the compressive force applied by the patient interface device on the surface of the skin, which, in turn, may effect the sealing characteristics of the patient interface device against the user.

It is envisioned that conduit coupling assembly 10 of the present invention may also be included as an integral part of a patient interface system 200 or patient interface device 202.

It is also envisioned that conduit coupling assembly 10 may also be used in connection with or retrofitted upon existing patient interface systems 200. In one embodiment, conduit coupling 212 includes a first end 230 and a second end 232. First 230 of conduit coupling 212 is attached to patient interface device 202, and second end 232 is in fluid communication with patient circuit 210. Patient interface system 200, which includes the conduit coupling assembly 10 of the present invention, operates as is known in the art.

With respect to the present invention, and as shown schematically in FIG. 1, conduit coupling assembly 10 includes a coupling retention assembly 12 and an adjustment assembly 14. Coupling retention assembly 12 retains the adjustment assembly 14 in a predetermined position with respect to the user's face A. Adjustment assembly 14 is in operable communication with conduit coupling 212 and permits adjustment of the position and orientation of conduit coupling 212. Further, conduit coupling 212 is continuously adjustable and retainable in an adjusted position and orientation by adjustment assembly 14, as well as coupling retention assembly 12. Details of various embodiments for coupling retention assembly 12 and an adjustment assembly 14 are discussed below.

Figure 2:
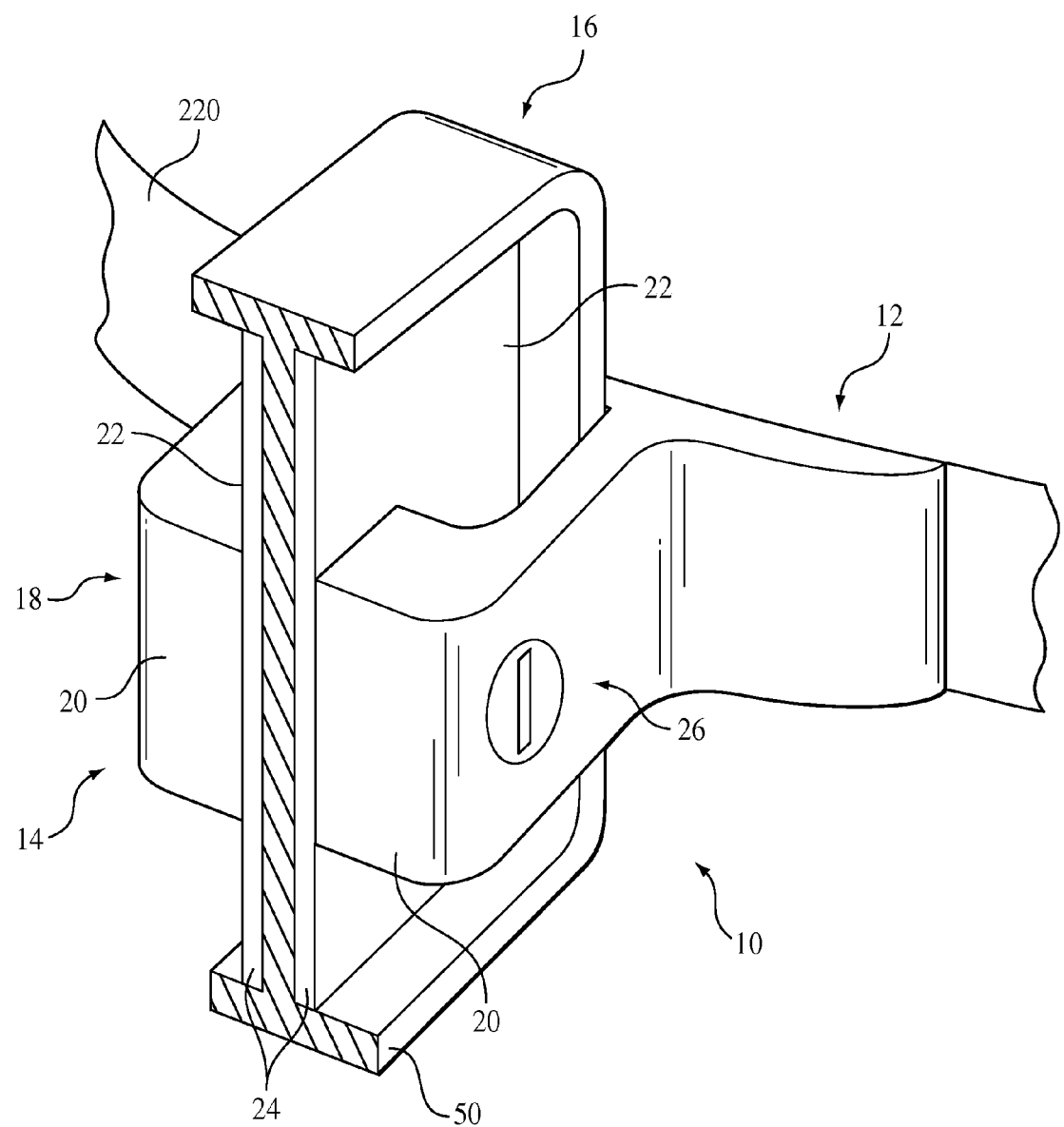
FIG. 2 is a perspective view of one embodiment of an adjustable conduit coupling assembly according to the principles of the present invention.

In one embodiment, adjustment assembly 14 includes a coupling collar 16, which is attached to a portion of conduit coupling 212. Such a coupling collar 16 is illustrated in FIGS. 2-7, however with respect to FIG. 2, conduit coupling 212 is not shown for clarity purposes. In the embodiment of FIG. 2, conduit coupling 212 is attached to coupling collar 16 in the cross-hatched region. Such an arrangement allows the position and orientation of conduit coupling 212 to be adjusted and set without any predetermined incremental position. Further, such an assembly provides adjustment without a set pivot point. Accordingly, conduit coupling 212 can be moved up, down, in and out and in any angular position within the premises defined by collar 16.

In this embodiment, adjustment assembly 14 includes a clamping mechanism 18. The clamping mechanism includes at least two clamp arms 20, and each clamp arm is capable of contacting a respective and opposing clamping surface 22 on coupling collar 16. Therefore, clamping mechanism 18 is operable to an open position, such that coupling collar 16 is movable, and a clamped position, such that coupling collar 16 is held in a specified position and orientation by clamping mechanism 18.

As shown in the embodiment of FIG. 2, coupling retention assembly 12 is mounted to or otherwise attached to a forehead strap 220 of headgear assembly 204. Therefore, the user need not move, orient or otherwise reposition coupling retention assembly 12 and forehead strap 220 in order to change the position and/or orientation of conduit coupling 212 relative to his or her head/face. Instead, using conduit coupling assembly 10, the user simply operates clamping mechanism 18 to an open position, adjusts coupling collar 16 within the now open champing arms (which adjusts the relative position of conduit coupling 212 on the user), and then operates clamping mechanism 18 to a closed position, thereby retaining the desired position.

In one embodiment, opposing clamping surfaces 22 of coupling collar 16 include a padded member 24, which provides a flexible contact surface for clamp arms 20. The padded member also allows for more secure clamping when the clamp arms are moved to the clamped position.

In order to maintain the clamped position, clamping mechanism 18 may also include a locking mechanism 26. Specifically, locking mechanism 26 retains clamp arms 20 in the clamped (closed) position and releases the clamp arms in the unclamped (opened) position, such that coupling collar 16 is movable between the clamp arms. Any number of locking mechanisms 26 are envisioned, such as a tackle clamp, a release button, a combination of a lever and a release button, a ratchet mechanism, a latch mechanism or other similar means for retaining the clamp arms in a clamped position. In one embodiment, a lever-operated locking mechanism 26 will include a lever with an approximate travel of 180°. In order to lock or clamp clamp arms 20, the lever is turned downward away from the user's forehead B. Any position in between the travel positions would allow the coupling collar 16 to move with restricted motion due to the friction for fine adjustment.

Figure 3:
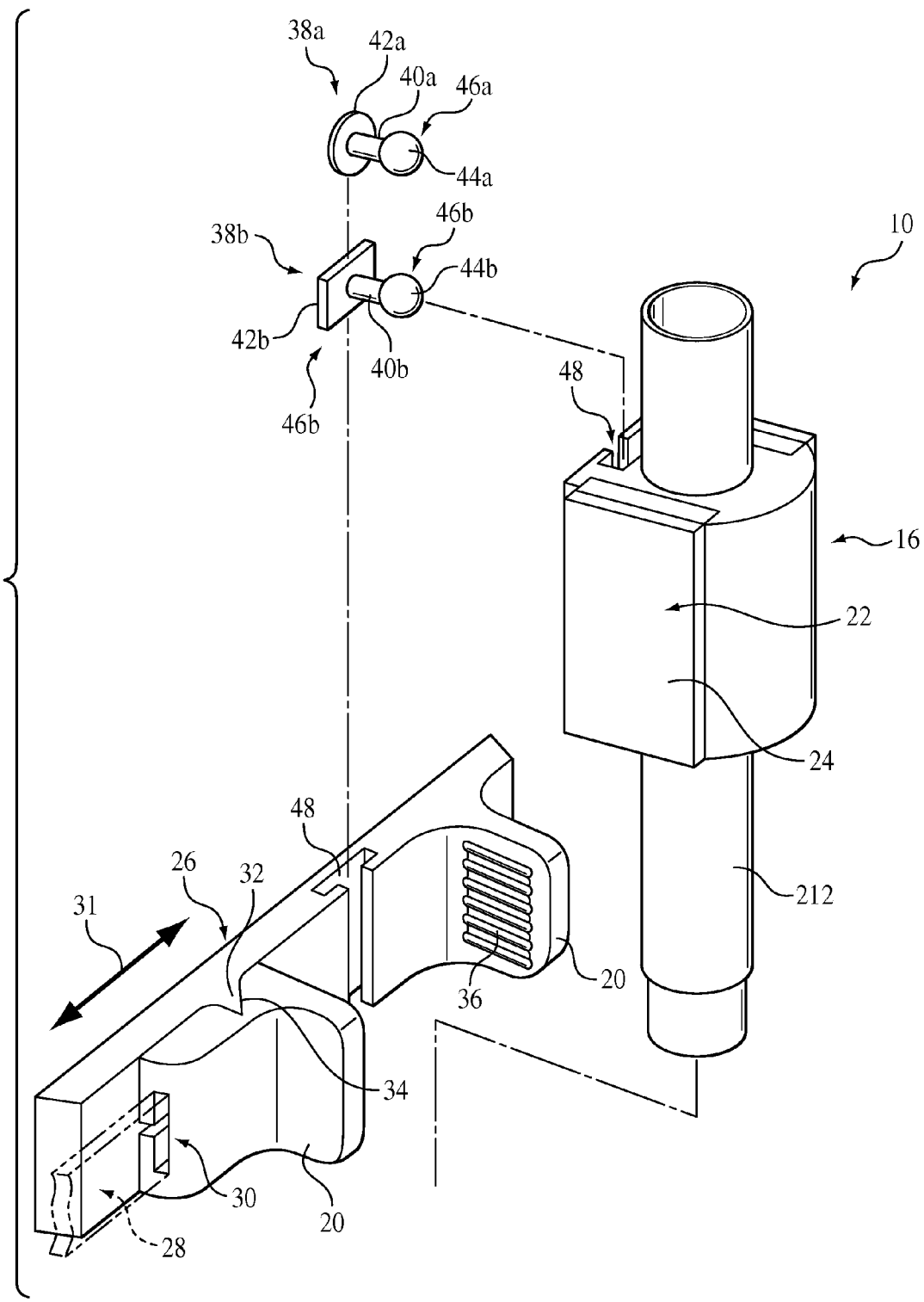
FIG. 3 is an exploded perspective view of another embodiment of an adjustable conduit coupling assembly according to the principles of the present invention.
Figure 4:
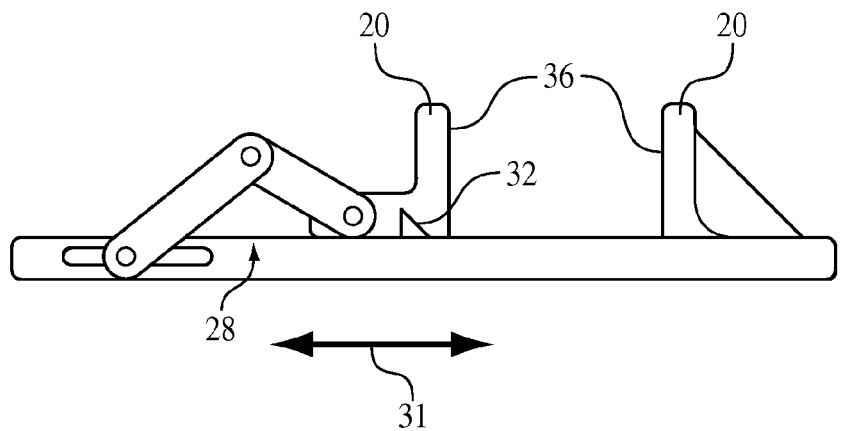
FIG. 4 is a plan view of a clamping mechanism used in connection with the adjustable conduit coupling assembly of FIG. 3.

In another embodiment shown in FIGS. 3 and 4, locking mechanism 26 includes a slide track 28, which allows at least one of clamp arms 20 to slide along the slide track between the open position and the clamped position. The sliding clamp arm includes a track engagement member 30 that slidingly engages slide track 28. Accordingly, clamp arm 20 is capable of being slid or moved along slide track 28, as indicated by arrow 31. While any number of movements is envisioned, in an exemplary embodiment, slide track 28 and track engagement member 30 allow for the substantial lateral movement of clamp arm 20 along the slide track.

Also, in this embodiment, locking mechanism 26 may also include one or more locking tabs 32. Locking tab 32 extends from slide track 28 and engages a complimentary recess 34 on the track engagement member 30. Recess 34 removably receives or mates with locking tab 32 for locking clamp arm 20 in a predetermined position. Of course, it is also envisioned that locking tab 32 may extend from track engagement member 30, and slide track 28 includes the complimentary recess 34 for engaging tab 32. Multiple tabs 32 (and recesses 34) may be used for varying positions of clamp arm 20.

In one embodiment, clamping mechanism 18 includes two clamp arms 20, and one of the clamp arms 20 is movable along slide track 28 via track engagement member 30, while the other clamp arm 20 is stationary. Of course, the present invention also contemplates providing the ability to move both clamp arms using this slide track configuration and its alternative. In order to provide a better gripping motion, one or both of clamp arms 20 includes an optional gripping surface 36 for enhancing the engagement characteristics between clamping surfaces 22 of coupling collar 16 and clamp arms 20.

In order to retain coupling collar 16 at or near clamping mechanism 18 when clamp arms 20 are in the opened position, a coupling collar retainer member 38a, 38b is utilized. In other words, the coupling collar retainer member prevents conduit coupling 212 from falling off the user once the clamping mechanism is loosened. Two different embodiments (38a and 38b) for the coupling collar retainer member are illustrated in FIG. 3

In a first embodiment, coupling collar retainer member 38a includes a coupler 40a having a first end 42a and a second end 44b. First end 42a is attached to locking mechanism 26 and/or coupling retention assembly 12, and second end 44a is attached to coupling collar 16. The first end and/or the second end of coupler 40a includes a track engagement member 46a attached thereto. Track engagement member 46a is sized and shaped so as to engage with a slide track 48 positioned on one or both of locking mechanism 26, coupling retention assembly 12, and/or coupling collar 16. Slide track 48 is disposed on both coupling retention assembly 12, as well as coupling collar 16. Accordingly, a track engagement member 46 may be positioned on both first end 42a and second end 44a of coupler 40a. In a second embodiment, coupler 40b is generally similar to coupler 40a, except for the configuration of first end 42b, which is configured to more closes conform to the cross-sectional shape of slide track 48.

Using this structure, coupler 40a or 40b can slide up and down with respect to both coupling retention assembly 12, as well as the coupling collar 16, when arms 20 are in the opened position. However, coupler 40a, 40b will also retain coupling collar 16, and, therefore, conduit coupling 212, through engagement of track engagement members 46a, 46b with slide tracks 48. In addition, track engagement members 46a, 46b and slide tracks 48 permit the user to freely adjust and reposition coupling collar 16, and hence conduit coupling 212, when clamp arms 20 are in the opened position. In one embodiment, coupler 40a, 40b is manufactured from a flexible material, such as rubber, silicone, a flexible synthetic material, etc. This allows more freedom of movement of coupling collar 16 when clamp arms 20 are in the opened position.

Figure 5:
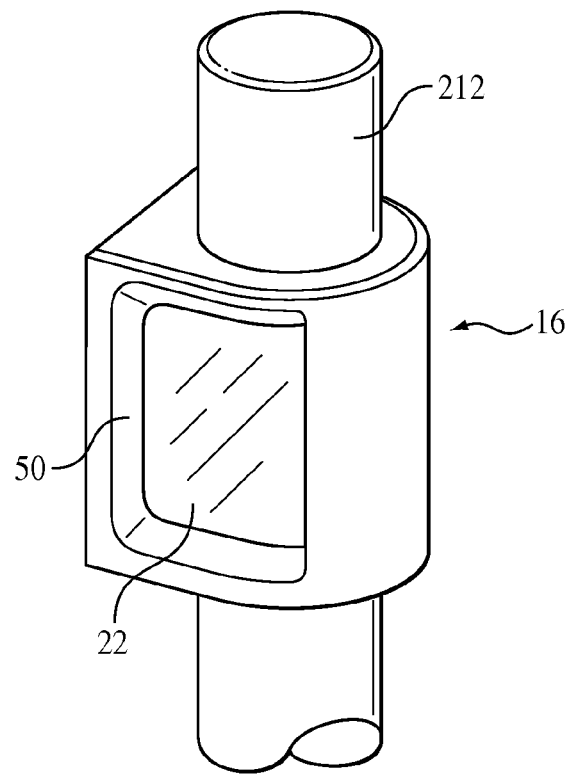
FIG. 5 is a perspective view of one embodiment of an coupling collar used in connection with the adjustable conduit coupling assembly according to the principles of the present invention.

Another technique for retaining coupling collar 16 when clamp arms 20 are in the opened position is illustrated in FIGS. 2 and 5. In this embodiment, coupling collar retainer member 38 is a rim 50 that extends from coupling collar 16 and is sized, such that when clamp arms 20 are in the opened position, the coupling collar cannot pass through the clamp arms, because the rim will contact a portion of the clamp arms. In operation, clamp arms 20 are opened, and coupling collar 16 is repositioned between the clamp arms. Next, the clamp arms are moved into the engaged or clamped position against clamping surfaces 22 of coupling collar 16. Collar retainer member 38 and/or rim 50 provide additional functionality for conduit coupling assembly 10, by allowing the user to adjust the system much closer to edges of collar 16.

Figure 6:
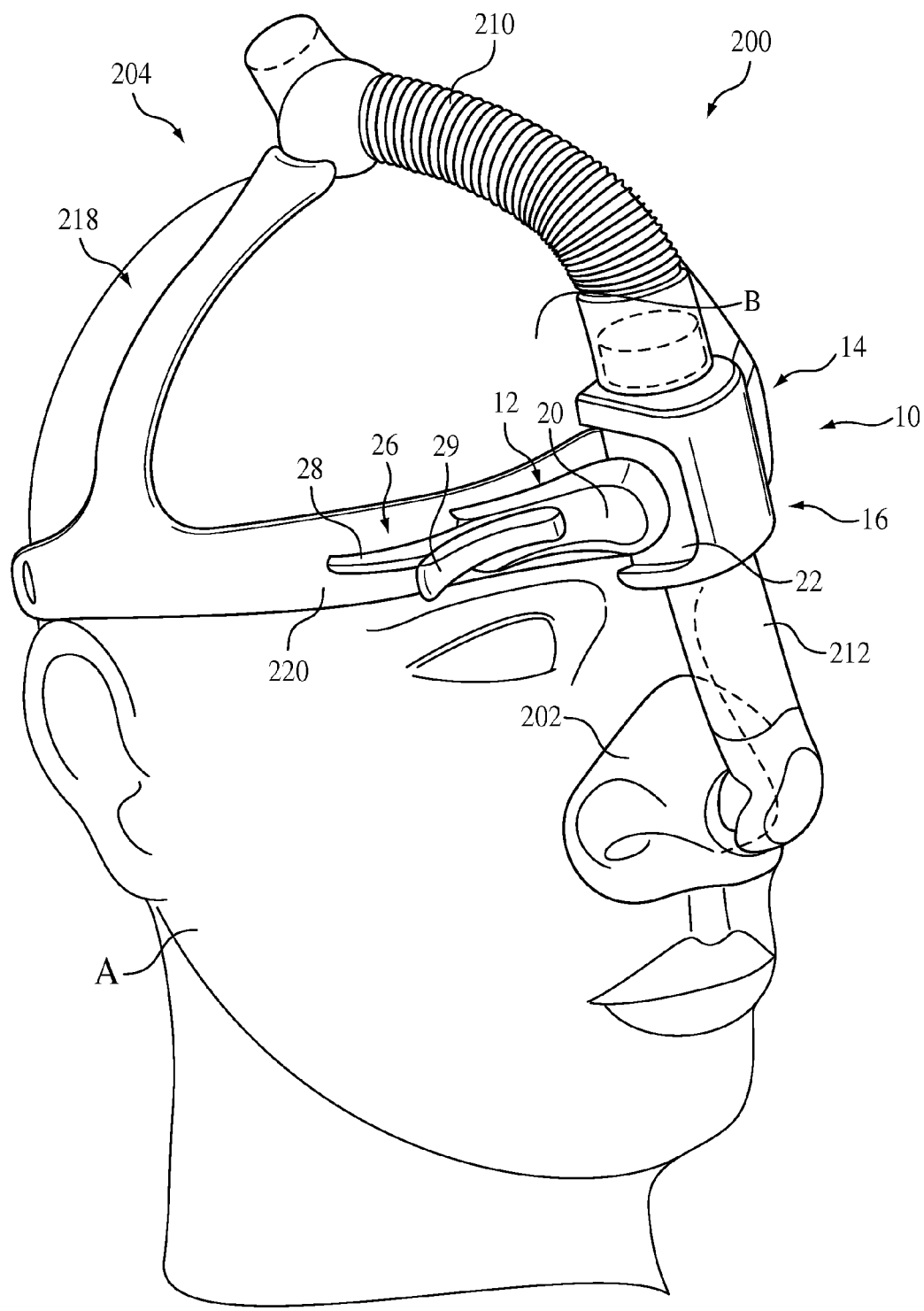
FIG. 6 is a perspective view of another embodiment of an adjustable conduit coupling assembly according to the principles of the present invention shown attached to a user via a headgear assembly.

FIG. 6. illustrates a slight variation of patient interface system 200. More specifically, this figures show a locking mechanism 26 that includes clamp arms 20 that slide along a track 28 defined in forehead strap 220. locking mechanisms 26 also includes a lever arm 29, in which a portion of the lever arm is moved toward the surface of the user to set the position of clamp arm 20 relative to forehead strap 220 using conventional level arm clamping techniques. Conversely, the clamp are is released so that it movers relative to the foreheads strap along track 28 by moving a portion of lever arm 29 away from the surface of the user.

Figure 7:
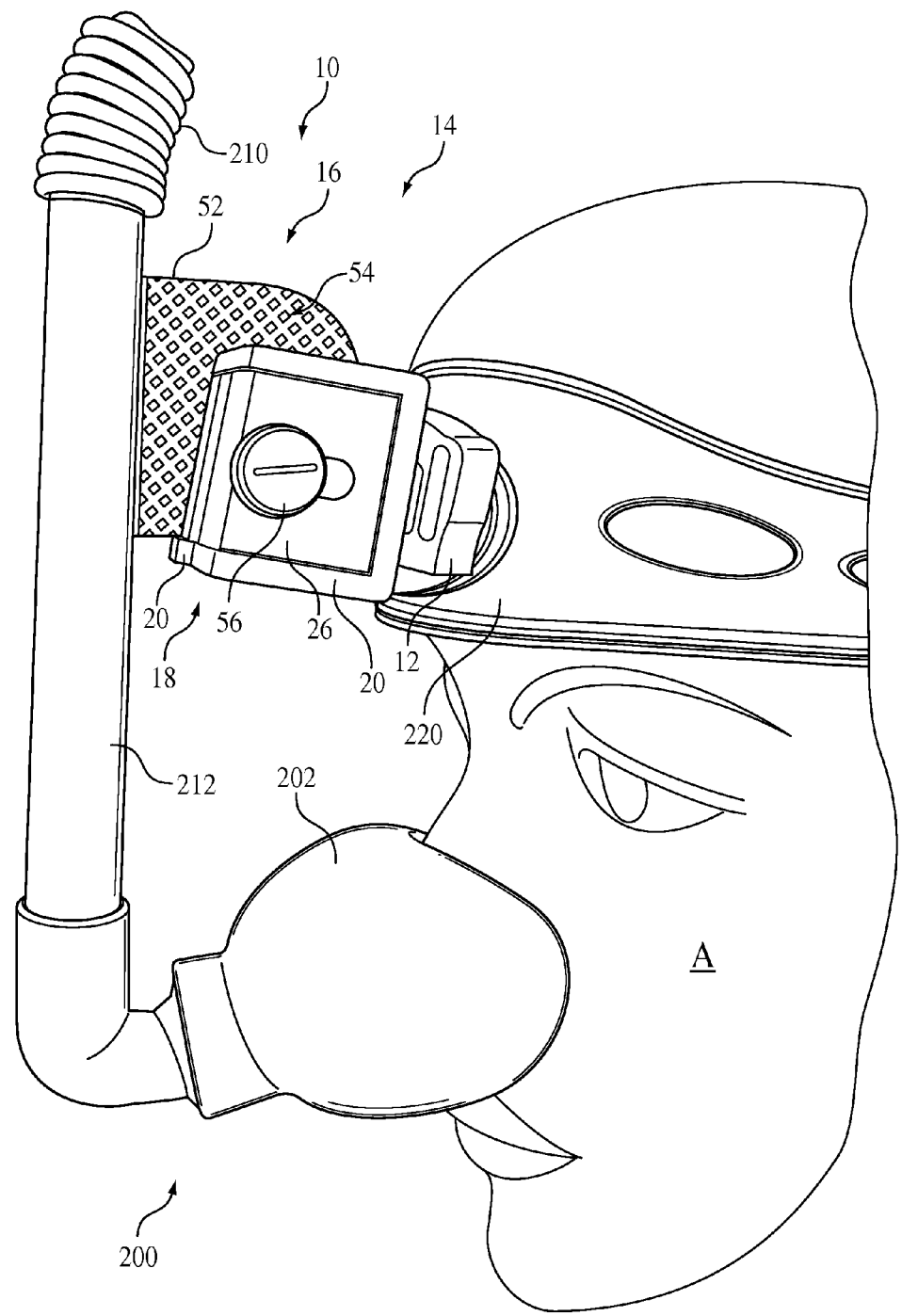
FIG. 7 is a perspective view of another embodiment of an adjustable conduit coupling assembly according to the principles of the present invention also shown attached to a user via a headgear assembly.

Yet another embodiment of a conduit coupling assembly 10 is illustrated in use in FIG. 7. In this embodiment, coupling collar 16 is a thin and substantially flat member 52 with a gripping surface 54 on either side of the flat member. Further, in this embodiment, locking mechanism 26 is a release button 56, which is positioned in opposition to some latching structure for use in disengaging this latching or clamping arrangement. Still further, in this embodiment, coupling collar 16, in the form of flat member 52, is attached directly to conduit coupling 212.

Figure 8:
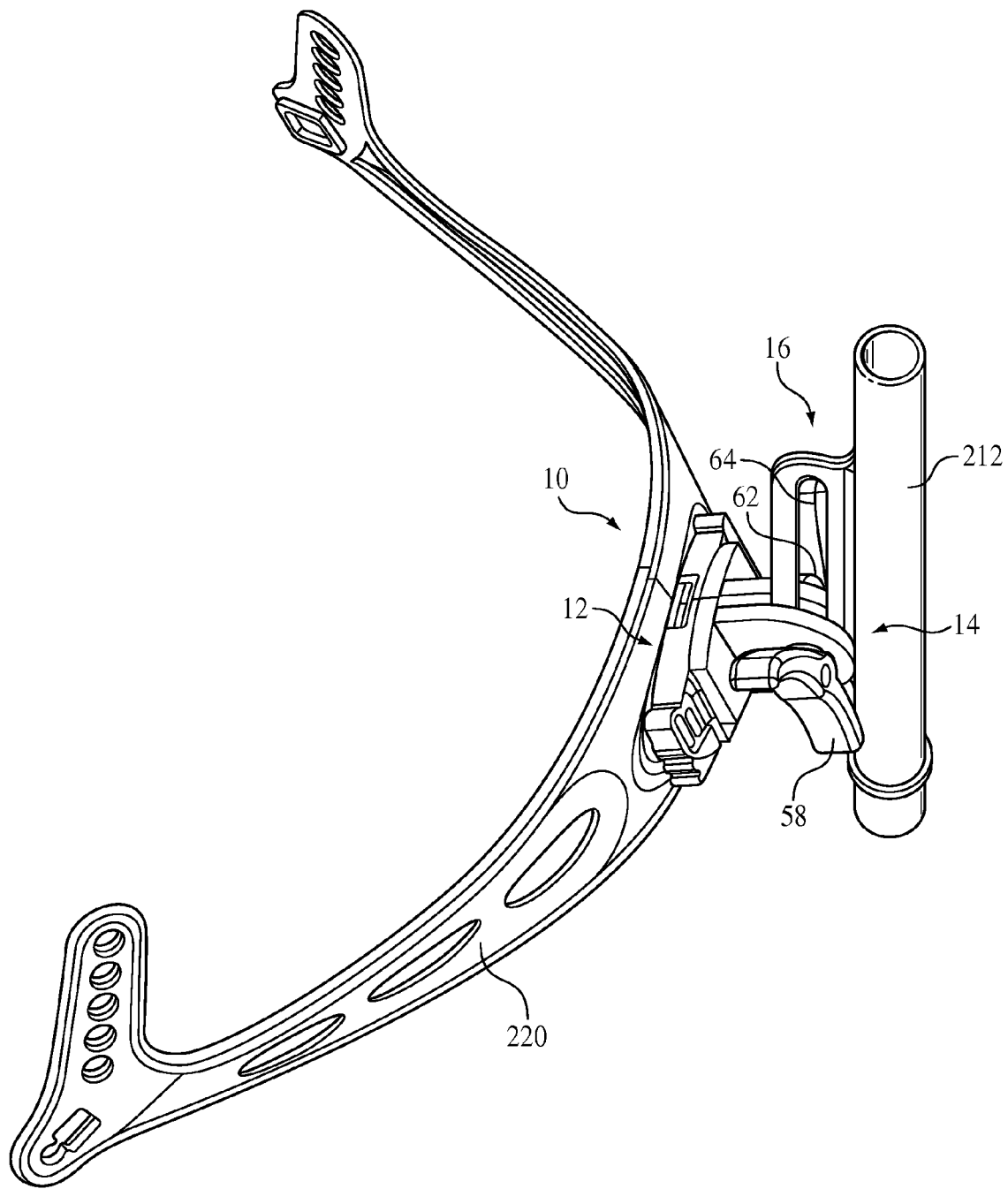
FIG. 8 is a perspective view of a further embodiment of an adjustable conduit coupling assembly according to the principles of the present invention.
Figure 9:
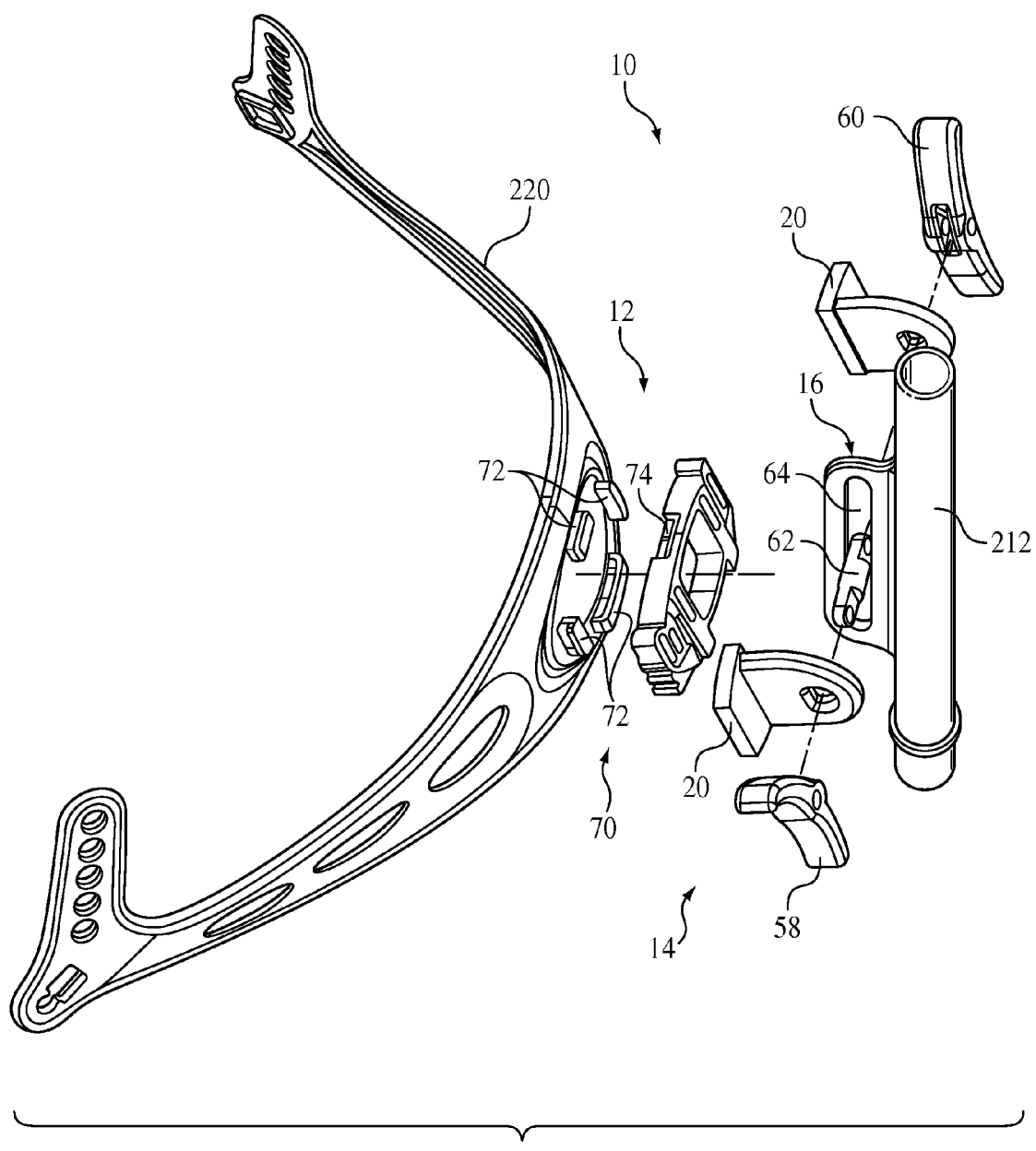
FIG. 9 is an exploded of the adjustable conduit coupling assembly of FIG. 8.

In still further embodiment of a conduit coupling assembly 10 is illustrated in FIGS. 8 and 9. In this embodiment, locking mechanism 26 in adjustment assembly 14 includes a first lever 58 in operational communication with one of clamp arms 20, as well as a second opposing lever 60 in operational communication with the other clamp arm. First lever 58 and second lever 60 are operable to urge clamp arms 20 to the clamped position, and to release the clamp arms to the opened position. Clamp arms 20 engage coupling collar 16 attached to conduit coupling 212.

Further, in this embodiment, first lever 58 and second lever 60 are attached by a connector member 62 extending through a slot 64. Slot 64 extends through coupling collar 16, such that connector member 62 is movable within slot 64 when clamp arms 20 are in the opened position. Specifically, using first lever 58 and second lever 60, clamp arms 20 are opened by pressing levers 58, 60 together. Next, coupling collar 16 (which is attached to conduit coupling 212) is moved to a desired position, at which point levers 58, 60 are released, and clamp arms 20 re-engaged in the clamped position.

While two levers are shown in the embodiment of FIGS. 8 and 9, it should be noted that only a single locking lever arrangement is also envisioned for use in opening and closing arms 20. Further, levers 58, 60 may be spring loaded and urged in a specific direction, or may be a rocking arrangement, with pressure applied at either the upper or lower portions of levers 58, 60 to engage and disengage the lock (as illustrated in FIGS. 8 and 9).

Also, in this embodiment, connector member 62 acts as coupling collar retainer member 38. In this manner, when clamp arms 20 are in the opened position, disconnection of coupling collar 16 from coupling retention assembly 12 is prevented by contact between connector member 62 and the edge of slot 64. Therefore, if the user accidentally releases coupling collar 16 and/or conduit coupling 212 during the repositioning maneuver, and while clamp arms 20 are in the opened position, coupling collar 16 will simply drop until contact is made between the end of slot 64 and connector member 62.

Figure 10:
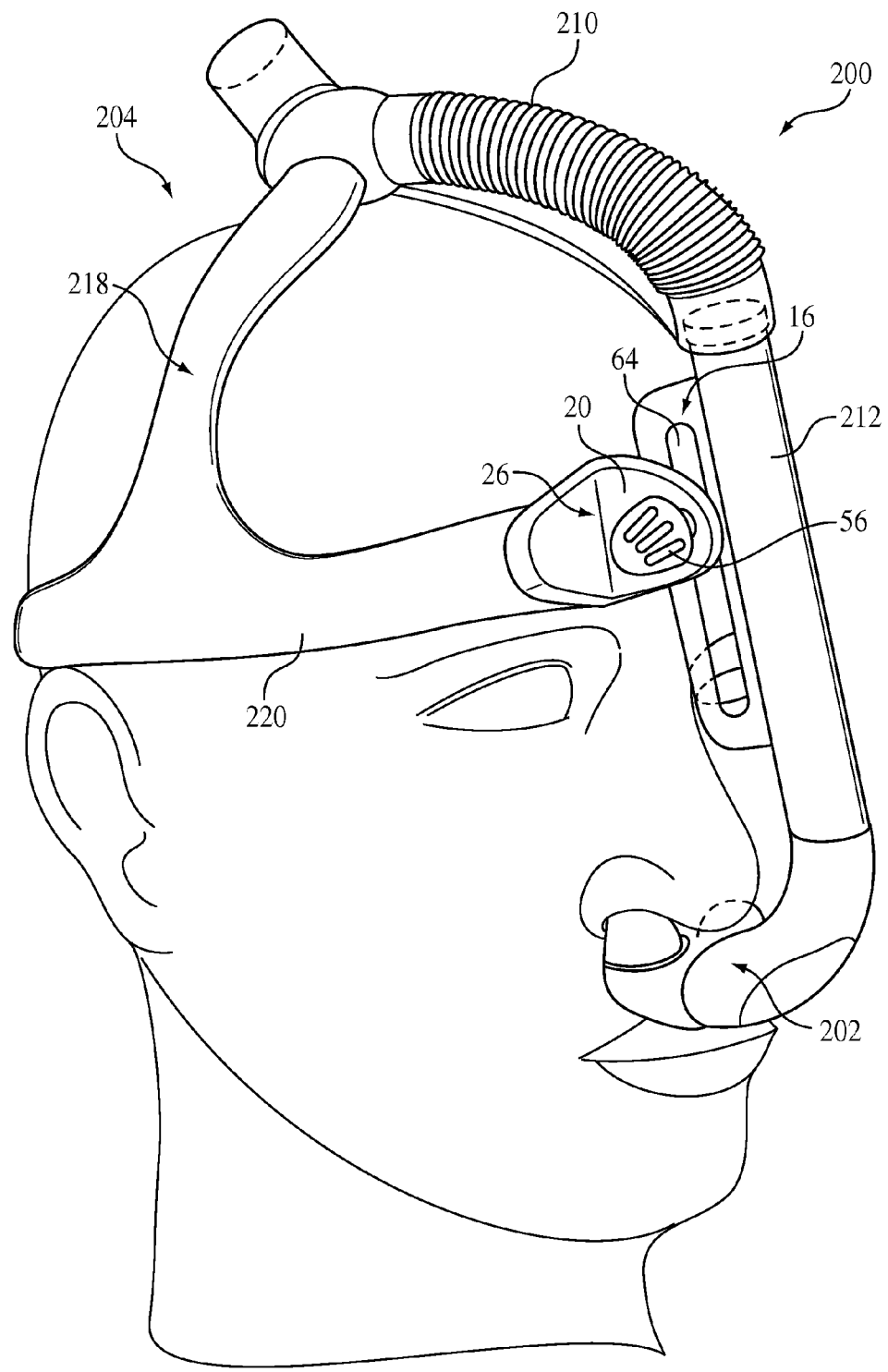
FIG. 10 is a perspective view of another embodiment of an adjustable conduit coupling assembly according to the principles of the present invention as attached to a user by a headgear assembly.

Another embodiment of conduit coupling assembly 10, which also illustrates slot 64 and connector member 62, is shown in FIG. 10. In this embodiment, release button 56 is used to release clamp arms 20 against a portion of the area adjacent slot 64. In addition, in this embodiment, patient interface device 202 is a nasal mask.

Figure 11:
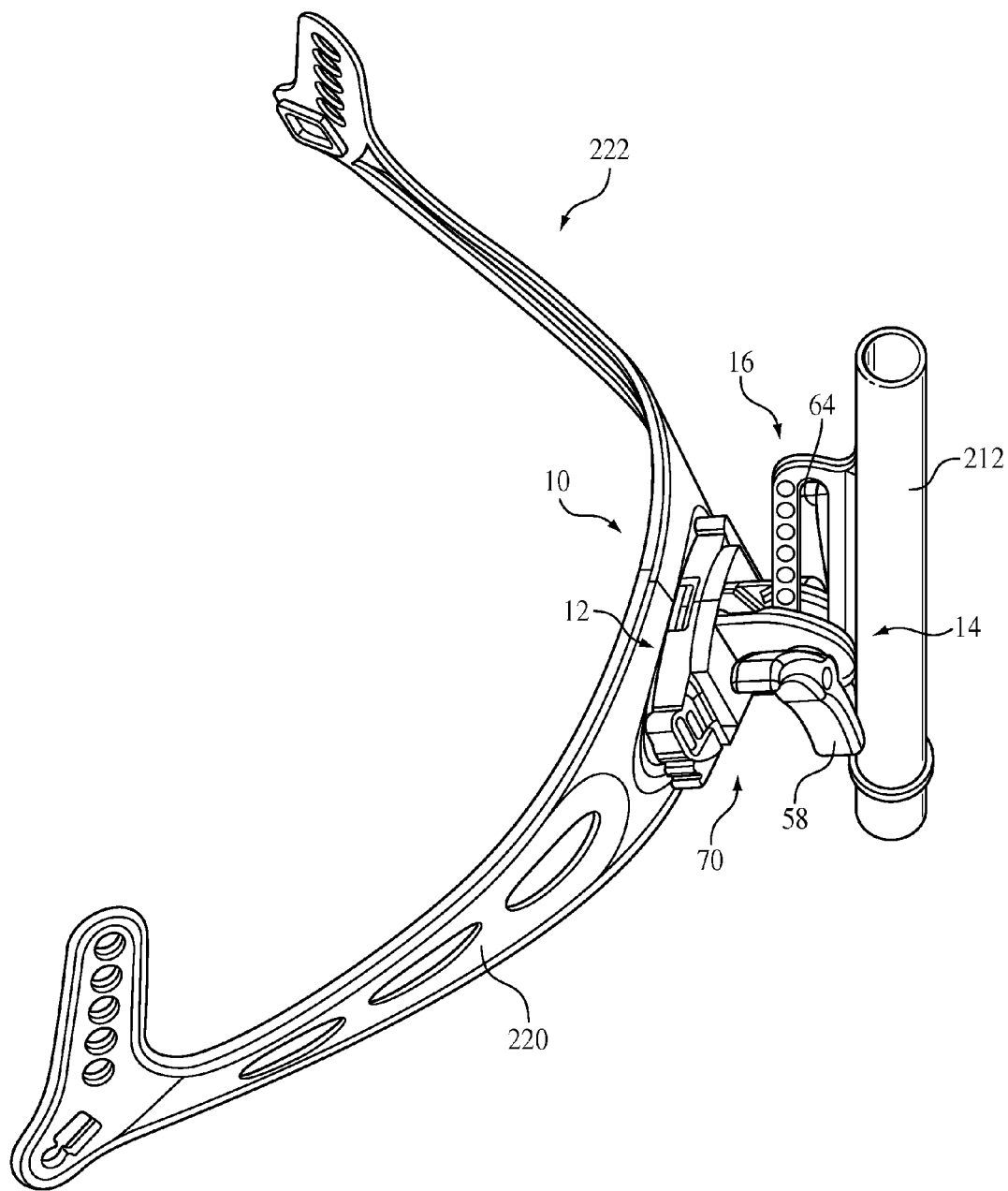
FIG. 11 is a perspective view of a further embodiment of an adjustable conduit coupling assembly according to the principles of the present invention.
Figure 12:
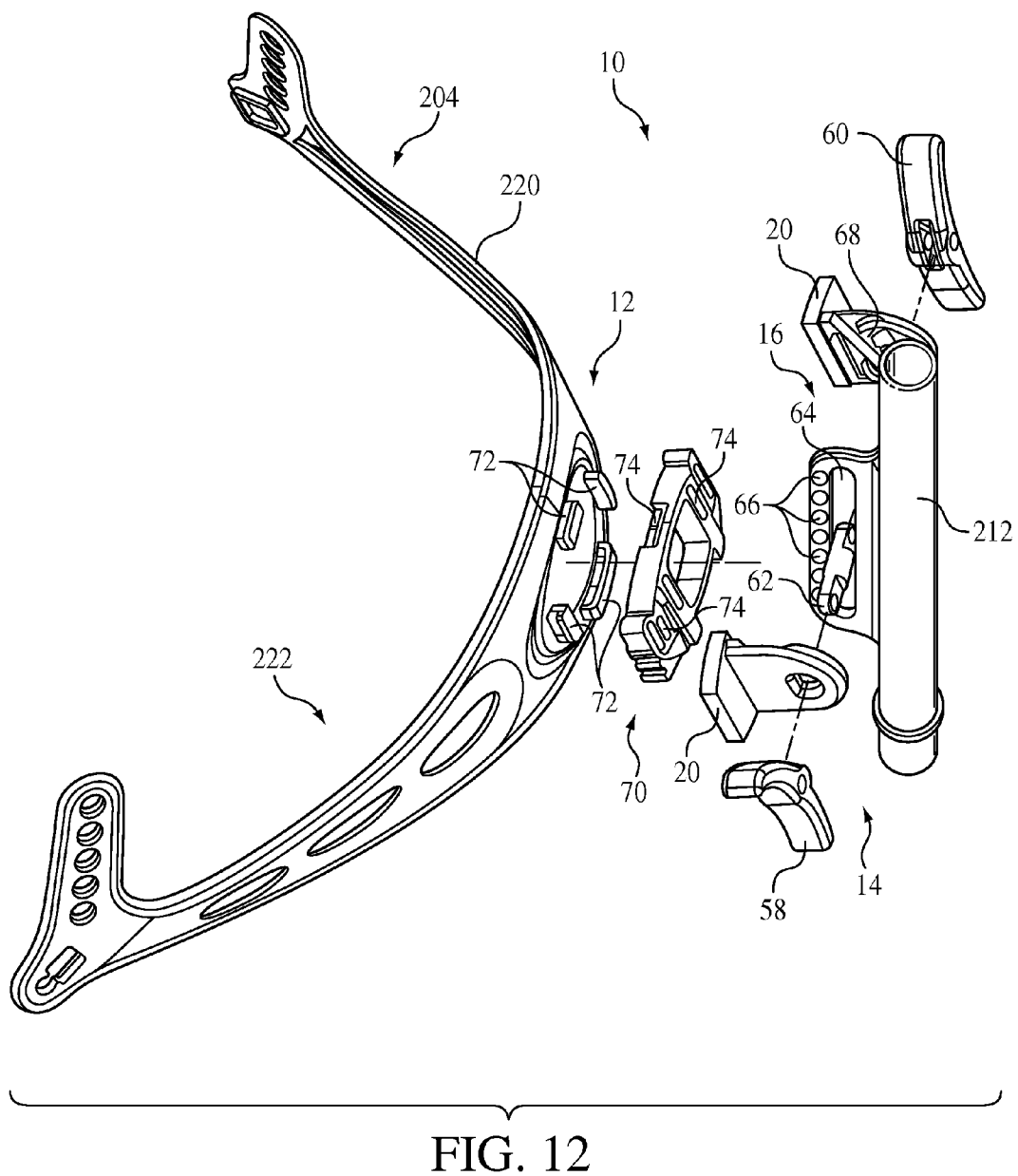
FIG. 12 is an exploded perspective view of the adjustable conduit coupling assembly of FIG. 11.

A still further embodiment of conduit coupling assembly 10 is illustrated in FIGS. 11 and 12. In this embodiment, coupling collar 16, and specifically an area adjacent slot 64, includes multiple projection sets 66 extending from the surface of the coupling collar. In operation, projection sets 66 slidingly engage a track 68 that is positioned on a surface of one or both of clamp arms 20. In operation, when clamp arms 20 are in the opened position, projection sets 66 are slidable along track 68 and positionable along this track in a specified set point to achieve a desired coupling collar position. In one preferred embodiment, projection sets 66 are spaced along and extend from the surface of the coupling collar, thereby providing multiple selectable positions. This structure allows the user to more easily manipulate coupling collar 16, and hence conduit coupling 212, when clamp arms 20 are in the opened position.

As best seen in FIGS. 9, 11, and 12, coupling retention assembly 12 may also include a removable retainer clip 70. This retainer clip is used to attach adjustment assembly 14, as well as conduit coupling 212, to headgear assembly 204, such as forehead strap 220. Any means of removably attaching retainer clip 70 to headgear assembly 204 is envisioned, such as through a series of projections and mating slots, clips, etc. For example, as shown in FIGS. 9, 11, and 12, headgear assembly 204 includes a headgear element 222. Retainer clip 70 and headgear element 222 include multiple projections 72, and retainer clip 70 and headgear element 222 also include a mating slot 74. Accordingly, projections 72 and mating slots 74 are engaged and disengaged to attach and remove retainer clip 70 to and from headgear element 222.

In a further embodiment of conduit coupling assembly 10, which is illustrated in FIGS. 13-16, adjustment assembly 14 includes a tilt assembly 76, an extension assembly 78, or both. Tilt assembly 76 allows the user to adjustably tilt conduit coupling 212 with respect to the user's face A, i.e., to move conduit coupling 212 with respect to a user's face such that the conduit coupling rotates in a plane that is parallel with a centerline of the user's face, as generally indicated arrow 77 in FIG. 16, i.e., about an axis defined by button 56. Extension assembly 78 allows the user to adjustably move conduit coupling 212 in a direction that is generally parallel to the centerline of the user's face, as generally indicated by arrow 79.

One exemplary embodiment of the use of tilt assembly 76 and extension assembly 78 is illustrated in FIGS. 13-16. In this embodiment, coupling retention assembly 12 includes arms 81 extending therefrom. Adjustment assembly 14 includes coupling collar 16 attached to conduit coupling 212, where coupling collar 16 is engageable with arms 81.

Figure 15:
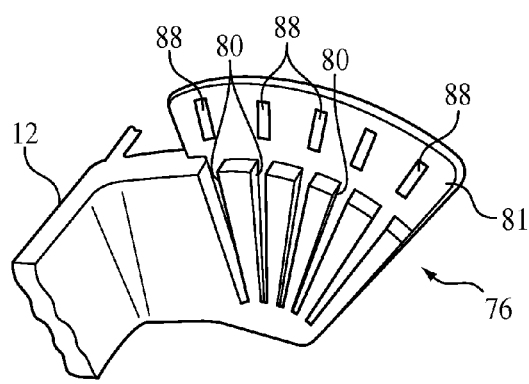
FIG. 15 is a perspective view of another portion of the adjustment assembly of FIG. 13.

Arms 81 include multiple slots 80 positioned along a surface of the arms. In addition, coupling collar 16 includes a track projection 82 extending from a surface of coupling collar 16. The track projection is capable of slidingly engaging one of the multiple slots 80 on arms 81. As best seen in FIG. 15, slots 80 of arms 20 extend at predetermined angles along the surface of the arms, thereby providing tilt assembly 76 with multiple and selectable tilt positions of coupling collar 16 and conduit coupling 212.

In this embodiment, locking mechanism 26 includes multiple latch arms 84 extending from coupling collar 16. Each of the latch arms includes a latch projection 86 extending therefrom. Further, arms 81 include multiple latch slots 88 positioned on a surface of each arm, and preferably in substantial alignment with each of slots 80. In operation, latch projection 86 of latch arm 84 is engageable and disengageable with latch slots 88, thus allowing movement of conduit coupling 212 relative to coupling retention assembly 12. In addition, latch arms 84 are releasable by the user by flexing the latch arms inward, as indicated by arrow 83, thereby engaging latch projections 86 with latch slots 88 and preventing further movement of conduit coupling 212, i.e., securing coupling collar 16 in coupling retention assembly 12.

Figure 13:
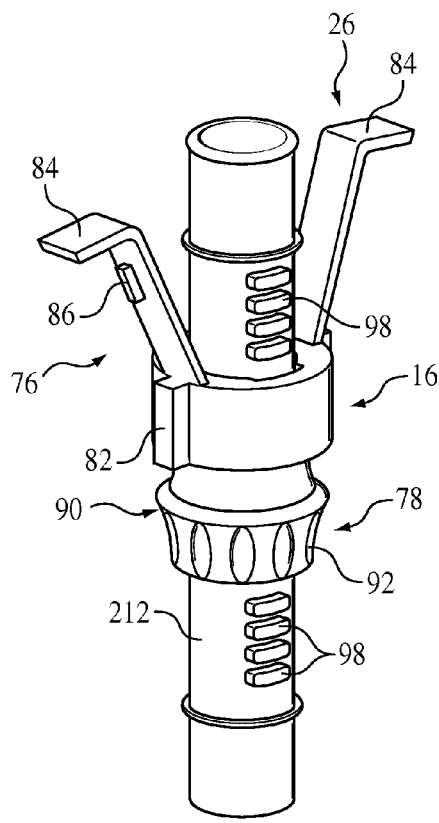
FIG. 13 is a perspective view of a portion of an adjustment assembly of a further embodiment of an adjustable conduit coupling assembly according to the principles of the present invention.
Figure 14:
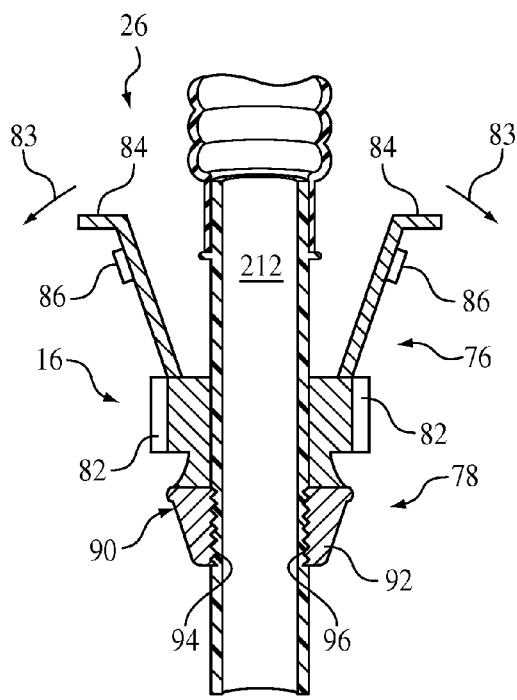
FIG. 14 is a sectional view of the portion of the adjustment assembly of FIG. 13.

This embodiment also illustrates an extension assembly 78 that includes an extension collar 90 that surrounds and is slidably engaged with conduit coupling 212. In particular, extension collar 90 is engageable with conduit coupling 212 to prevent sliding thereof, and is disengageable with conduit coupling 212 to allow sliding thereof. Therefore, extension collar 90 allows adjustable and lateral positioning of conduit coupling 212. As best seen in FIGS. 13 and 14, extension collar 90 includes a nut 92 with an inner orifice 94 with threads 96 disposed thereon. Further, conduit coupling 212 includes multiple thread tracks 98 positioned on a surface of conduit coupling 212. These thread tracks are sized and shaped so as to mate with threads 96 on inner orifice 94 of nut 92. In this manner, nut 92 can be rotated to adjust the lateral position of conduit coupling 212. It is envisioned that the lateral positioning of conduit coupling 212 may also effect a movement of conduit 210, or alternatively is slidable within conduit 210, where the conduit would be attached to latch arms 84.

Figure 16:
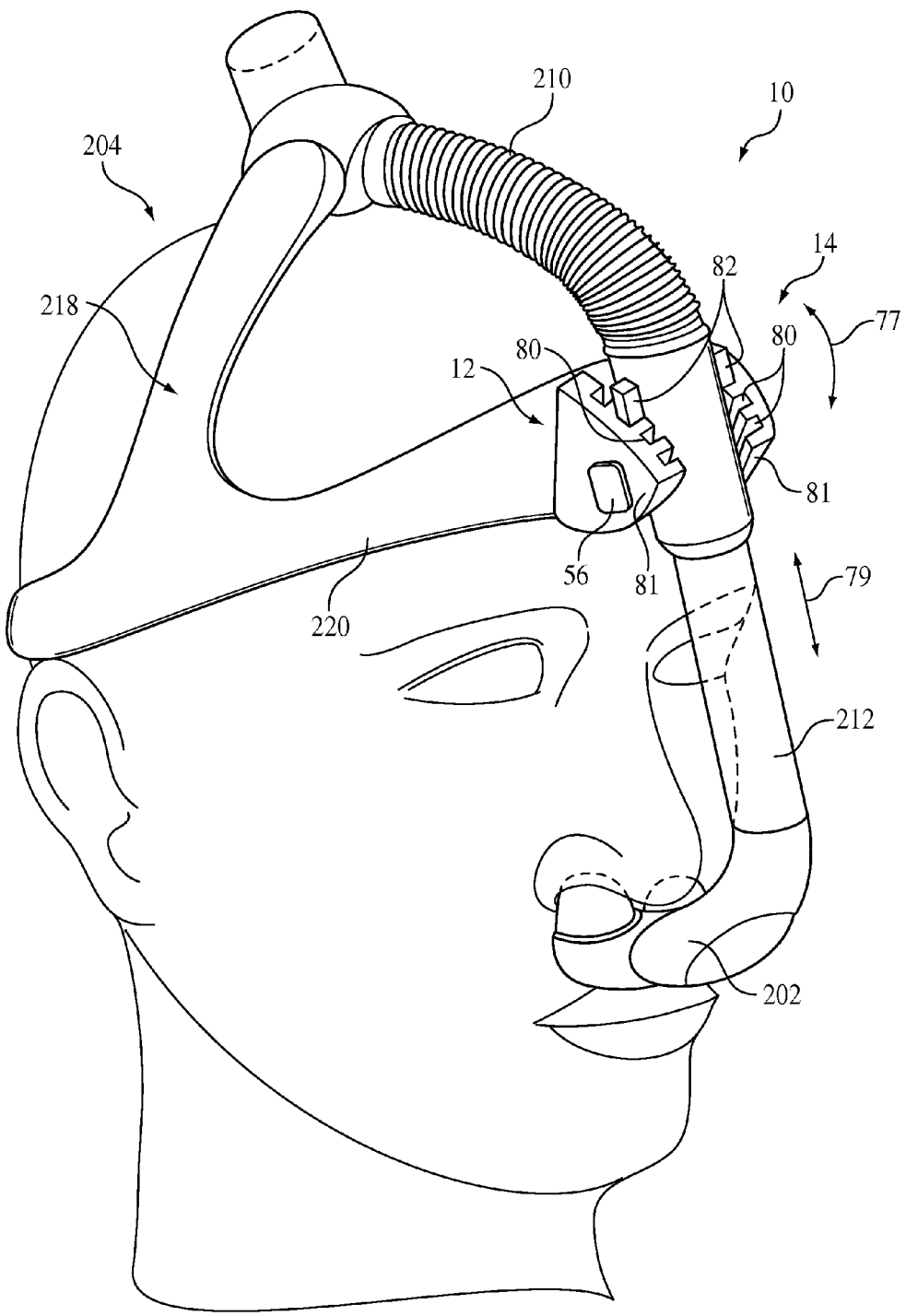
FIG. 16 is a perspective view of still further embodiment of an adjustable conduit coupling assembly according to the principles of the present invention shown attached to a user by a headgear assembly.

In the embodiment illustrated in FIG. 16, tilt assembly 76 includes track projections 82 and slots 80. Locking mechanism 26 does not include latch arms 84 discussed above, but is a simple release button 56 or the like. In an exemplary embodiment of the present invention, button 56 is a mechanical lock that functions based on principle similar to that of latch arm 84. That is button 56 is a spring loaded detent attached to conduit coupling 212 that engages an opening provided in arm 81 when the conduit coupling is properly attached to arms 81 to retain the conduit coupling in an engaged relation with arms 81. This configuration is more compact than that of FIGS. 13-15 and be concealed within the clamp body. Locking of the track projections in slots 80 can be achieved by a friction engagement therebetween.

Figure 17:
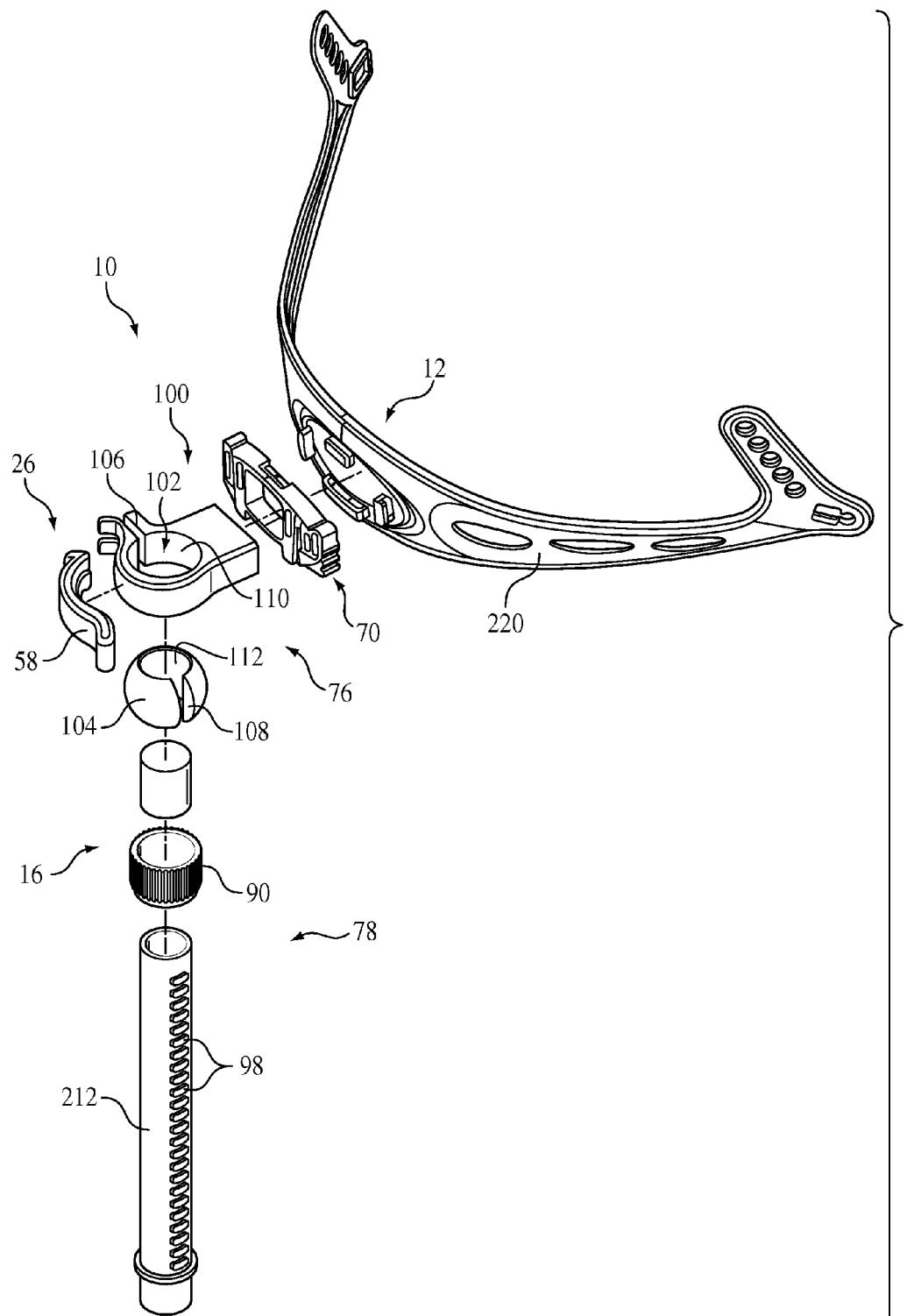
FIG. 17 is an exploded perspective view of another embodiment of an adjustable conduit coupling assembly according to the principles of the present invention.
Figure 18:
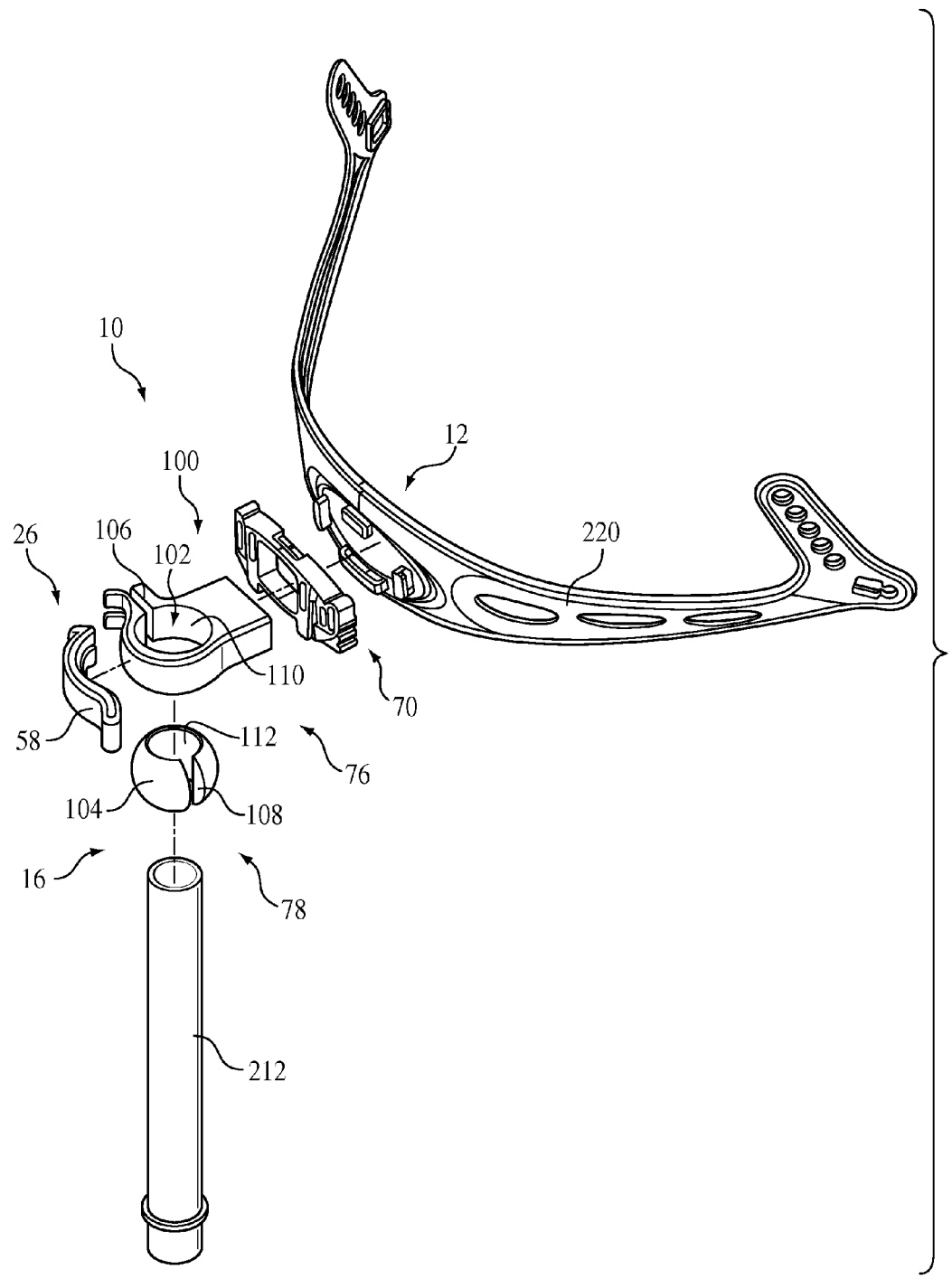
FIG. 18 is an exploded perspective view of a further embodiment of an adjustable conduit coupling assembly according to the principles of the present invention.
Figure 19:
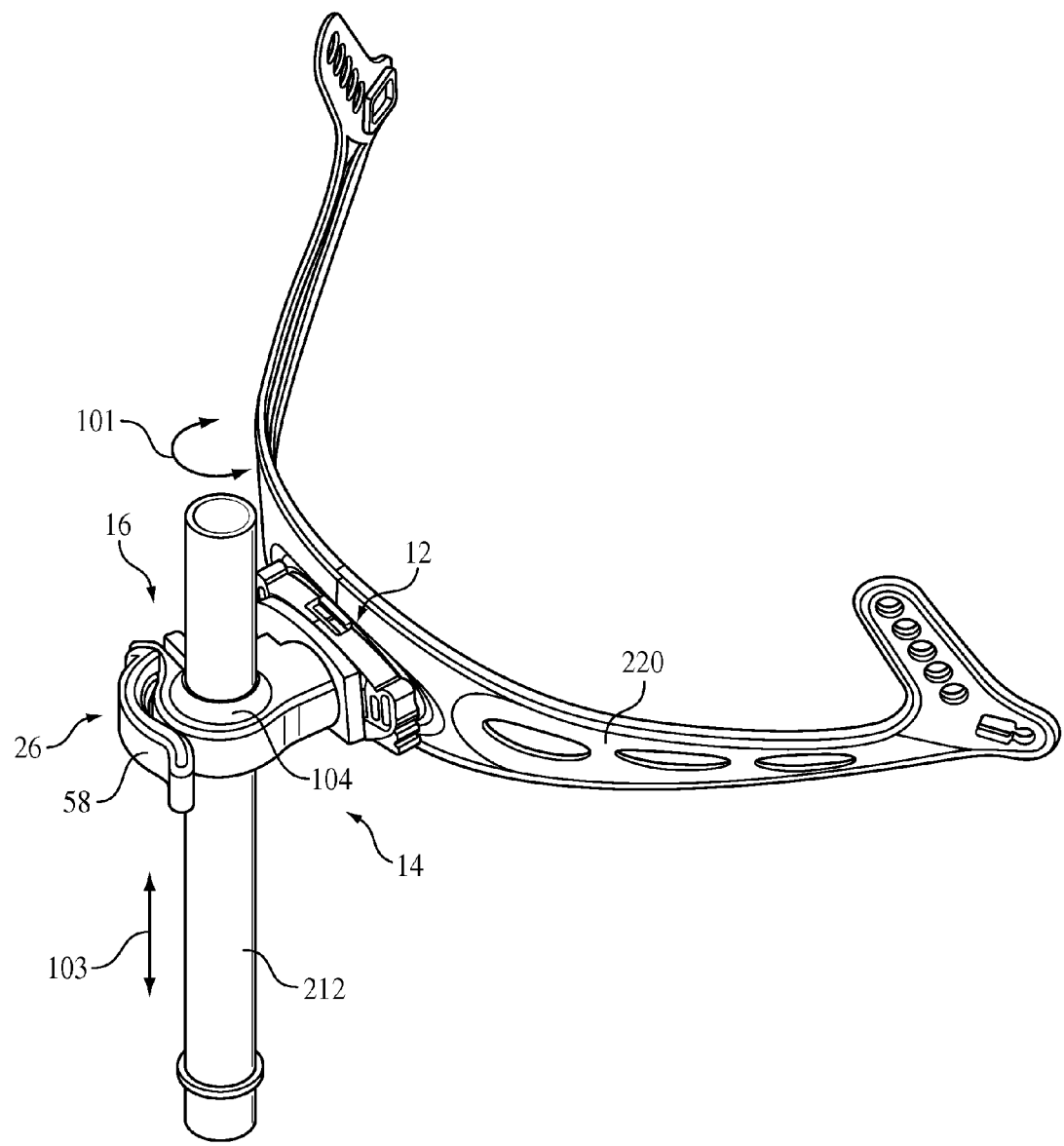
FIG. 19 is a perspective view of the adjustable conduit coupling assembly of FIG. 18.
Figure 20A:
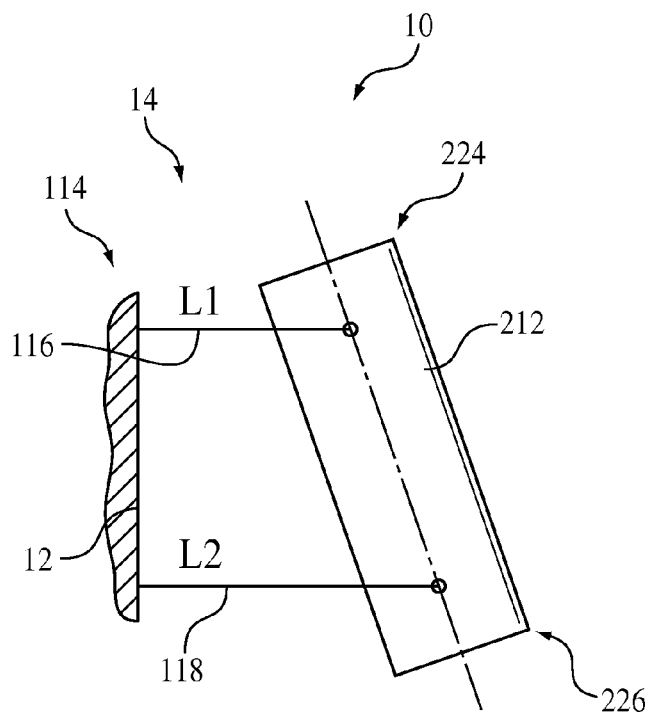
FIGS. 20A and 20B are a schematic views of a further embodiment of an adjustable conduit coupling assembly according to the principles of the present invention shown in two different positions.
Figure 20B:
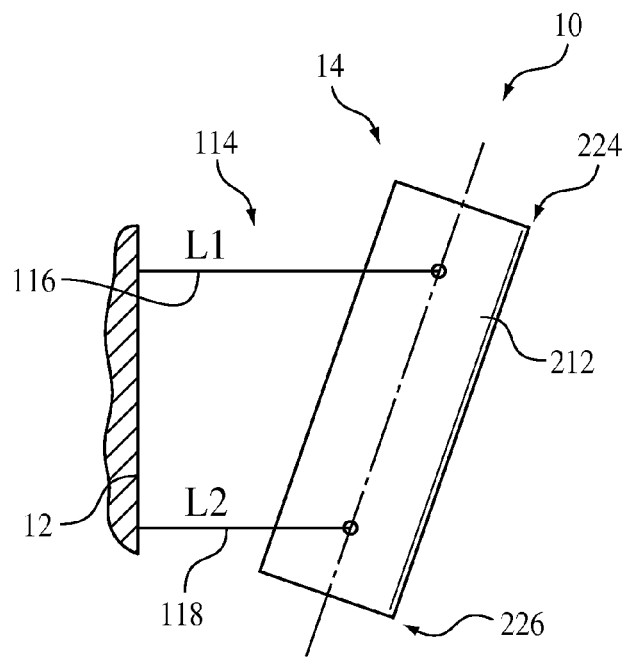

Yet another embodiment of conduit coupling assembly 10 is illustrated in FIGS. 17-19. In this embodiment, coupling retention assembly 12 includes a tilt arm 100 with a tilt arm orifice 102 extending therethrough. Further, in this embodiment, coupling collar 16 includes a rounded surface 104, which is positionable within tilt arm orifice 102, as well as slidable along conduit coupling 212. Accordingly, tilt arm orifice 102 is adjustable around coupling collar 16 between a clamped position and an open position.

As best seen in FIGS. 17 and 18, and in one embodiment, tilt arm 100 includes a split portion 106 that allows tilt arm orifice 102 to be adjustable between a clamped position and an open position. Specifically, by compressing the split portion 106 and releasing split portion 106, tilt arm orifice 102 decreases and increases in diameter to clamp and release conduit coupling 212, and specifically coupling collar 16. This compression and release is achieved via a locking mechanism 26 of any of the designs discussed above. In the structures illustrated in FIGS. 17-19, locking mechanism 26 includes a lever 58 that can be flipped open to decompress split portion 106, and flipped close to compress the split portion. Therefore, lever 58 is movably connected to tilt arm 100 for effecting the compression and release of split portion 106. By providing rounded surface 104 operatively coupled to conduit coupling 212, the conduit coupling is able to move in multiple axis and rotate within tilt arm 100, as indicated by arrow 101.

It is also envisioned that coupling collar 16 also includes a split portion 108. In this manner, coupling collar 16 is adjustable between an open position, where coupling collar 16 is slidable along conduit coupling 212, as indicated by arrow 103, and a clamped position, where coupling collar 16 is engaged against conduit coupling 212, thereby preventing movement of the conduit coupling relative to tilt arm 100. As discussed above, the compression and release of split portion 108 of coupling collar 16 is also implemented through the compression and release of tilt arm orifice 102 on tilt arm 100. Still further, it is envisioned that coupling collar 16 could be comprised of two halves, which could be spatially separated and secured within the arrangement, which would allow for easier installation and removal.

As with the rounded surface 104 of the coupling collar 16, the tilt arm orifice 102 may also include a rounded surface 110. In particular, rounded surface 110 of tilt arm orifice 102 mates with and interacts with rounded surface 104 of coupling collar 16. This provides a releasable and adjustable tilt assembly 76. Further, conduit coupling 212 is slidable along and through coupling collar 16, and in particular a coupling collar orifice 112. In this manner, a releasable and adjustable extension assembly 78 is provided.

In another embodiment, extension assembly 78 includes extension collar 90 discuss above with respect to FIGS. 13 and 14. Extension collar 90 is engageable and disengageable with conduit coupling 212, such that the conduit coupling is slidingly adjustable in a lateral position. As with the embodiments of FIGS. 13-15, extension collar 90 of this embodiment may be in the form of the above-discussed nut 92, which threads against thread tracks 98 on conduit coupling 212 surface. However, such a structure is not required, as evidence in the embodiments of FIGS. 18 and 19. In one embodiment, extension assembly 78 and coupling collar 16 are attached together or integrally formed together, such that extension assembly 78 and coupling collar 16 are a unitary piece.

Yet another embodiment of conduit coupling assembly 10 according to the principles of the present invention is illustrated in FIGS. 20A-24. In this embodiment, conduit coupling assembly 10 includes an adjustment assembly 14 that includes tilt assembly 76 for adjustably tilting the conduit coupling 212 with respect to the user's face A, i.e., in a manner discussed above with respect to FIG. 16, as indicated by arrow 77. However, in this embodiment, tilt assembly 76 includes multiple and adjustable pivot members 114. These pivot members 114 are in contact with and operable to move a respective portion of conduit coupling 212, thereby providing an adjustable tilt assembly 76. As seen in FIGS. 20A-23, a first pivot member 116 and a second pivot member 118 contact and are operable to move a respective first portion 224 of the conduit coupling 212 and a second portion 226 of the conduit coupling 212.

The present invention contemplates that any suitable connection can be provided between first pivot member 116 and conduit coupling 212, as well as between second pivot member 118 and conduit coupling 212. Examples of such connections include, but are note limited to, a rotatable hinge, a ball-and-socket attachment, a living hinge, etc. Adjustable pivot members 114 may be fixed directly to conduit coupling 212. In operation, first pivot member 116 expands and contracts over a distance L1 to push and pull first portion 224 of conduit coupling 212. Similarly, second pivot member 118 expands and contracts over a distance L2 to push and pull second portion 226 of conduit coupling 212. Accordingly, conduit coupling 212 is tilted to a desired position. If the sum of L1 and L2 is constant, then conduit coupling 212 pivots about a set and predetermined point. However, it is envisioned that L1 and L2 may be allowed to change in length within a separate and independent range, such that there is no set pivot point, which provides additional adjustability.

As best seen in FIGS. 22A-24, coupling retention assembly 12 may include the above-discussed tilt arm 100 with tilt arm orifice 102 extending therethrough. However, in this embodiment, tilt arm 100 need not include a split portion. In this embodiment, conduit coupling 212 is inserted through the arm orifice 102 of tilt arm 100. First pivot member 116 is positioned above tilt arm 100, and second pivot member 118 is positioned below tilt arm 100. Accordingly, conduit coupling 212 is tiltable or pivotable about tilt arm 100.

Figure 21A:
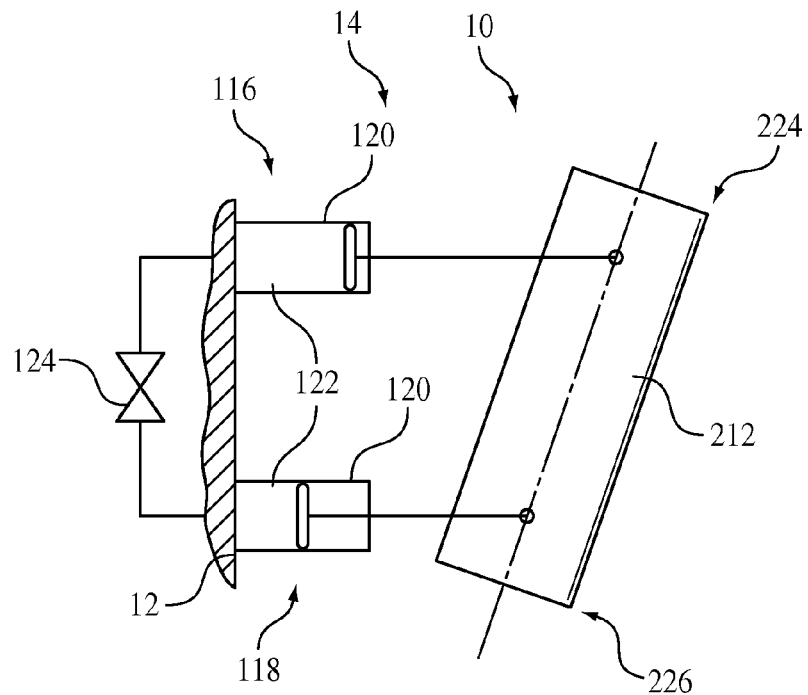
FIGS. 21A and 21B are schematic views of a still further embodiment of an adjustable conduit coupling assembly according to the principles of the present invention shown in two different positions.
Figure 21B:
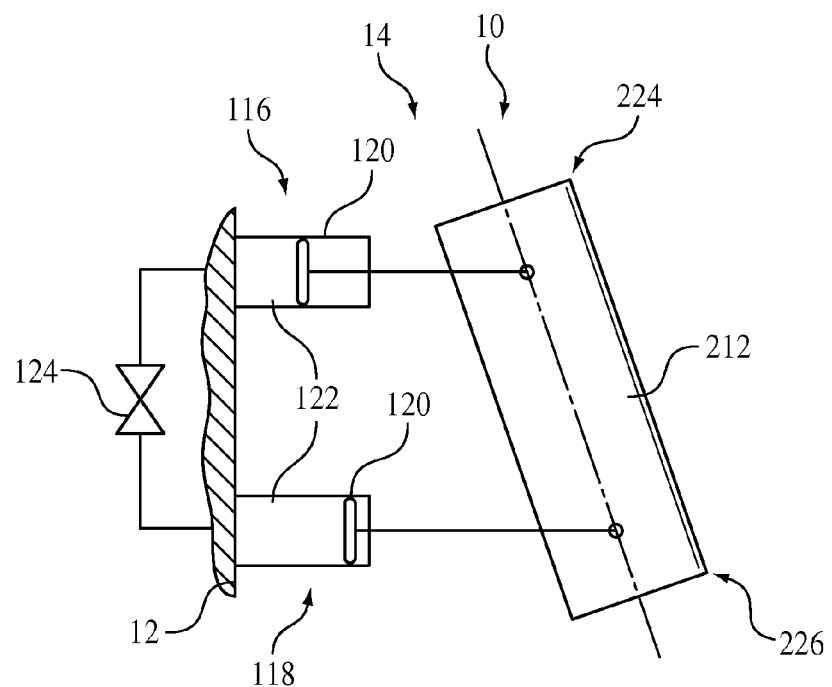
Figure 22A:
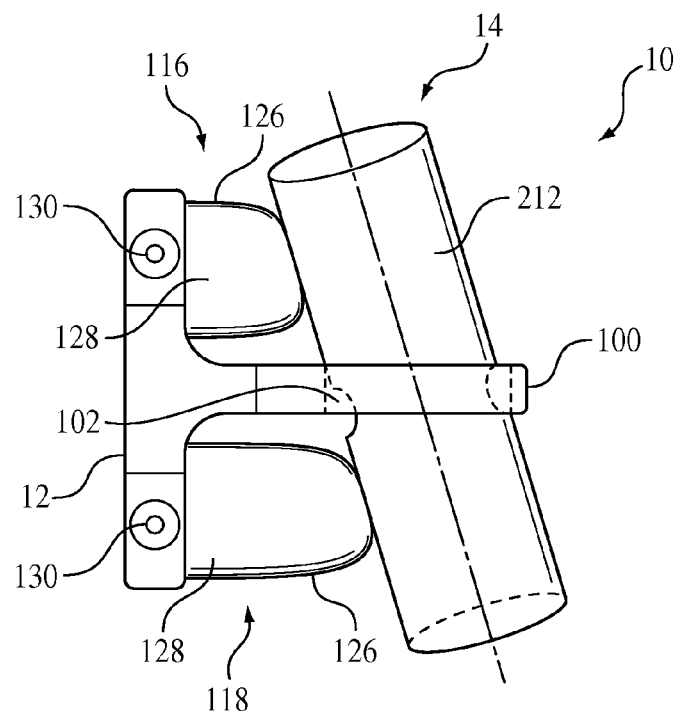
FIGS. 22A and 22B are schematic views of another embodiment of an adjustable conduit coupling assembly according to the principles of the present invention shown in two different positions.
Figure 22B:
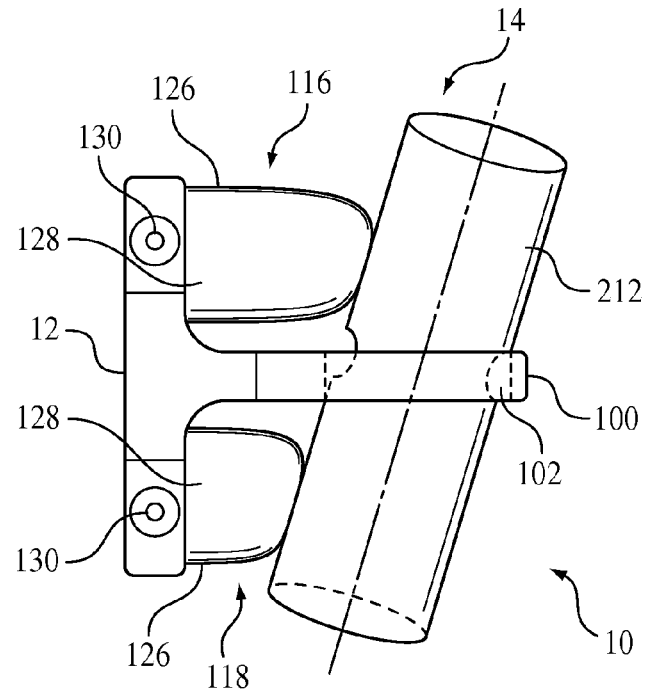

In the embodiment illustrated in FIGS. 21A and 21B, adjustable pivot members 116 and 118 are pistons 120 operable to extend and retract through insertion and removal of a material to and from a piston chamber 122. For example, the material may be a gas, a liquid material, etc. Also, the pivot members, or pistons 120, may be pneumatic pistons, where the material inserted into and removed from piston chambers 122 is air. In particular, the air is inserted through a valve 124 in fluid communication with an air source (not shown).

In a further embodiment, and as illustrated in FIGS. 22A-24, pivot members 116, 118 are bladders 126 which, similar to pistons 120, are operable to extend and contract through insertion and removal of a material to and from a bladder chamber 128. Again, the material may be a gas or a liquid material. In one embodiment, the material is air, and the air is inserted and removed from bladder chambers 128 through an air inlet 130 in fluid communication with an air pump 132. See FIGS. 23 and 24. Air pump 132 may be a user-operable hand pump or other mechanism to insert and withdraw air from bladder chambers 128. As discussed above, pistons 120 and/or bladders 126, may be filled or injected with any amount of material or medium, such that L1 and L2 are variable without any set pivot point.

Figure 23:
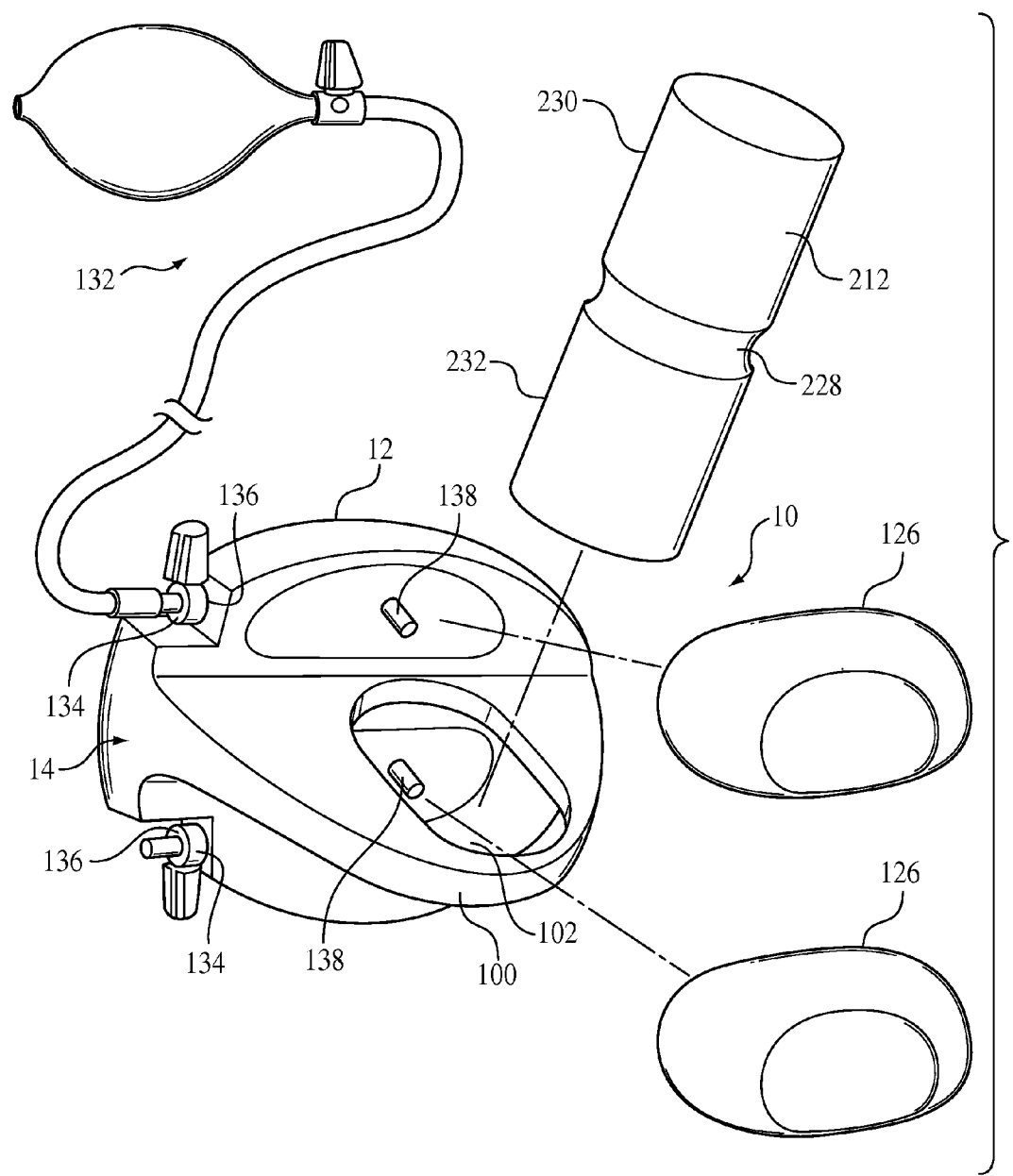
FIG. 23 is an exploded perspective view of the adjustable conduit coupling assembly of FIG. 22.
Figure 24:
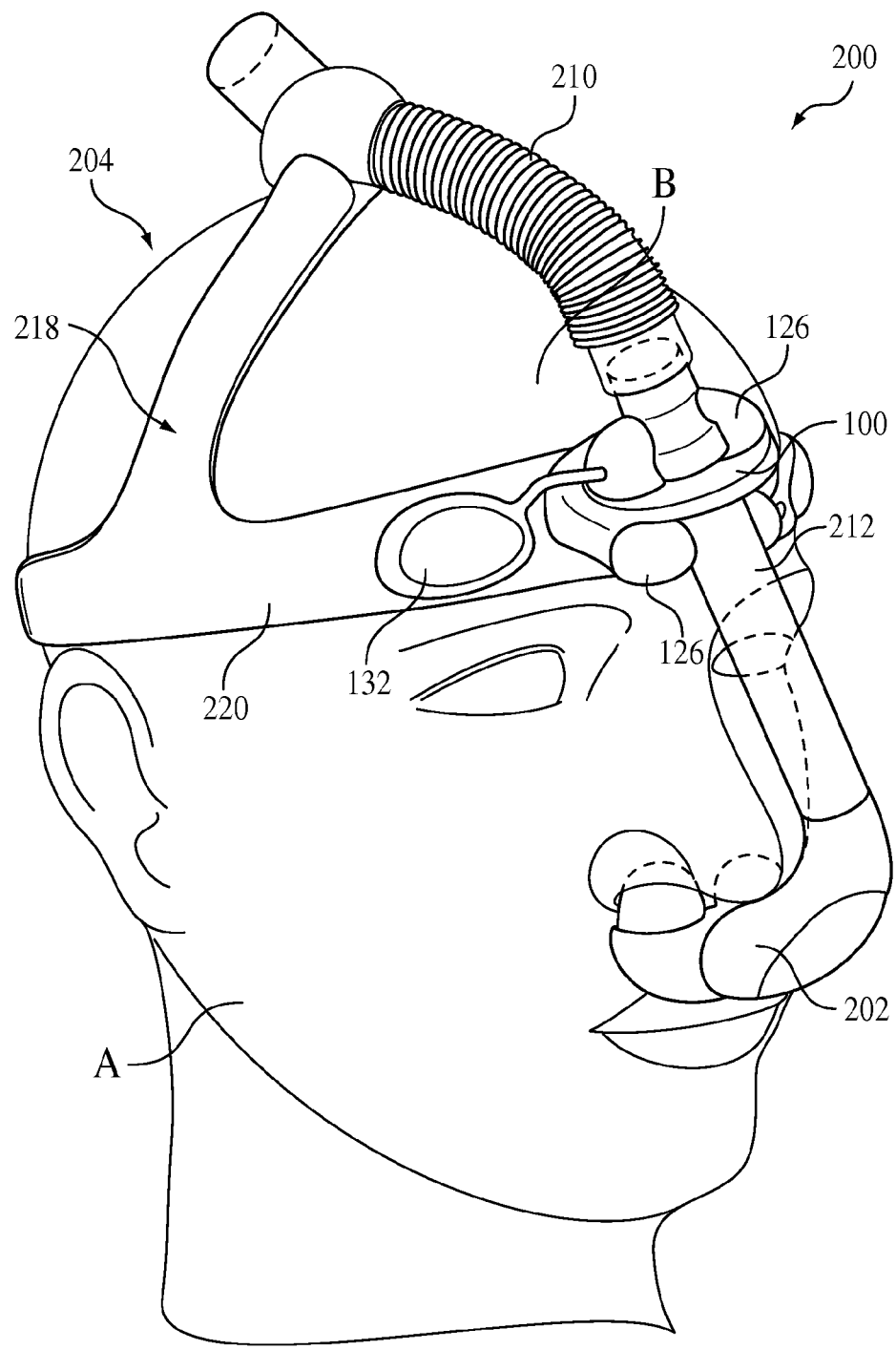
FIG. 24 is a perspective view of the adjustable conduit coupling assembly of FIG. 23 shown attached to a user via a headgear assembly.
Figure 25:
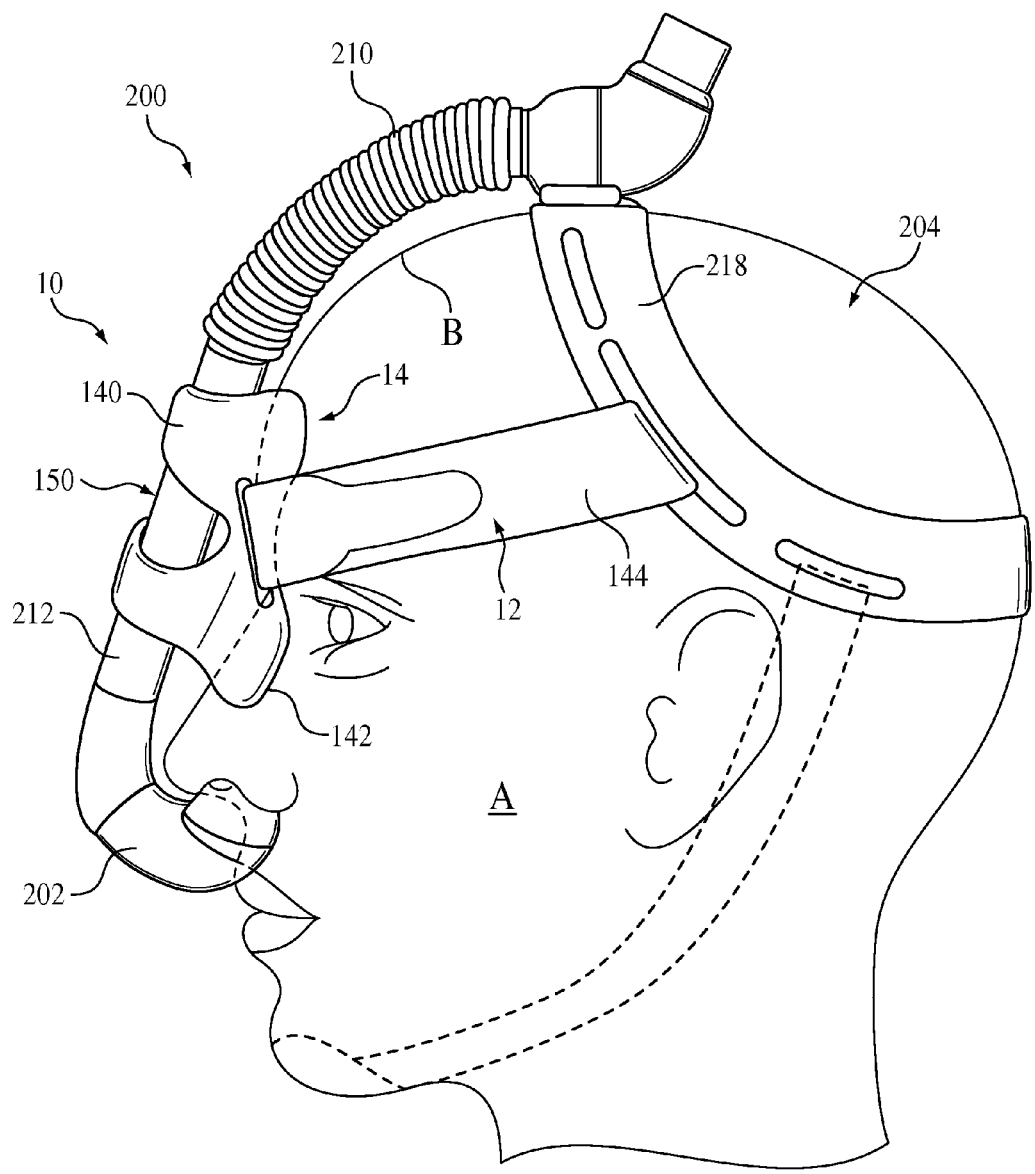
FIG. 25 is a side view of a still further embodiment of an adjustable conduit coupling assembly according to the principles of the present invention shown attached to a user via a headgear assembly.

As best seen in FIGS. 23 and 24, a material inlet 134 and a material outlet 136 are provided. Material inlet 134 allows or permits insertion of the material into bladder chambers 128, and material outlet 136 allows or permits removal of the material from bladder chambers 128. For example, an air pump 132 can be connected to the material inlet 134 for inserting air into the bladder chamber 128, and this same material inlet 134 may also be used as a material outlet 136 to release the air. Of course, the material inlet 134 and material outlet 136 can be an air release valve, a one-way valve and other similar structures, as known in the art.

Air pump 132 may easily be connected to material inlets 134, and each inlet 134 is connected to a respective bladder 126. It is also envisioned that the coupling retention assembly 12 and/or the adjustment assembly 14 include appropriate and fully communicating pathways, such that the air introduced from the air pump 132 flows through such pathways and into respective bladders 126. For example, as seen in FIG. 23, each bladder 126 can be engaged with a bladder inlet 138, which may also serve as an attachment mechanism. In any case, bladders 126 are engaged with a bladder inlet 138, which is in fluid communication with material inlets 134 and/or the material outlets 136.

Still further, in this embodiment, conduit coupling 212 includes a groove 228 extending around at least a portion of conduit coupling 212. However, in an exemplary embodiment, the groove extends around the entire perimeter of the conduit coupling. Groove 228 is positioned adjacent tilt arm orifice 102, and allows for better tilting and pivoting characteristics, which, in turn, allows for more fine adjustment of the conduit coupling 212. Groove 228 also improves the engagement between conduit coupling 212 and tilt arm orifice 102 and provides a fixed pivoting reference. The groove, as shown, is substantially narrower than the diameter of tilt arm orifice 102 so that conduit coupling 212 can freely move over a relatively large range within the tilt arm orifice. Groove 228 also helps to retain conduit coupling 212 in position in adjustment assembly 14. The present invention also contemplates eliminating the groove altogether, as the function of controlling the position of the conduit coupling will work perfectly well even without the groove.

It is also envisioned that the conduit coupling 212 be slidable through and retainable within tilt arm orifice 102. This allows for the adjustable and lateral positioning of conduit coupling 212 with respect to the user's face A. Accordingly, it is envisioned that conduit coupling 212 include multiple grooves 228 disposed along the surface of the conduit coupling 212 and engageable within tilt arm orifice 102.

In yet another embodiment of the present invention, which is illustrated in FIGS. 25-28, adjustment assembly 14 of conduit coupling assembly 10 includes a contact member 140 attached to conduit coupling 212. Contact member 140 includes a contoured adjustment surface 142 for contacting the user's face A and/or the user's forehead B. Movement and re-contact of contoured adjustment surface 142 on the surface of the user serves to adjust the position and orientation of conduit coupling 212 relative to the user. Contact member 140 may be a cushioned, pliable, or flexible member, such that contour adjustment surface 142 is conformal upon the user's face. Accordingly, contact member 140 may be foam, viscoelastic foam, a fillable cushion, a gel-filled cushion, an air-filled cushion, a silicon material, rubber, an elastomeric material, a pliable material, a flexible material, or any combination thereof.

In the illustrated exemplary embodiment, and as best seen in FIGS. 25-28, coupling retention assembly 12 may include one or more straps 144 attachable between contact member 140 and headgear assembly 204. Straps 144 retain patient interface device 202 in a sealed position on the user's face A through further connection with the headgear assembly 204.

Straps 144 may be adjustable and/or removable, thereby adjustably and removably attaching contact member 140 to the user's face. In addition, conduit coupling 212 may be laterally adjustable with respect to contact member 140. Still further, contact member 140 may be manufactured from a variety of materials and in a variety of shapes and sizes in order to maximize comfort and adjustability. For example, contact member 140 may be manufactured from multiple pieces, or include a cutout 150 or center opening, which, when the contact member is manufactured from a flexible material, allows it to form an angular support to the face A, since the flexible nature of the contact member and the cutout will flex to change the angular position.

Contact member 140 is configured such that a top portion 151 and a bottom portion 153 are defined in each side of cutout 150 and openings are defined in the top portion and the bottom portion. Conduit coupling 212 is inserted through the openings defined in top portion 151 and bottom portion 152. Conduit coupling 212 can slide up and down in contact member 140 so that the position of the conduit coupling in the contact member can be adjusted. The present invention also contemplates that a frictional fit can be provided between the conduit coupling and the contact member to provide some degree of locking of the conduit coupling relative to the contact member. In addition, a slight degree of resistance between the conduit coupling and the contact member provides a resilient feel for fine adjustment between these two member. Conduit coupling 212 will lock in position when contact member 140 is tightened by strap 144, because the deformation of a top portion 151 and a bottom portion 153 of contact member 140 resulting from the tightening of the strap will lock the conduit coupling in place on the contact member.

Figure 26:
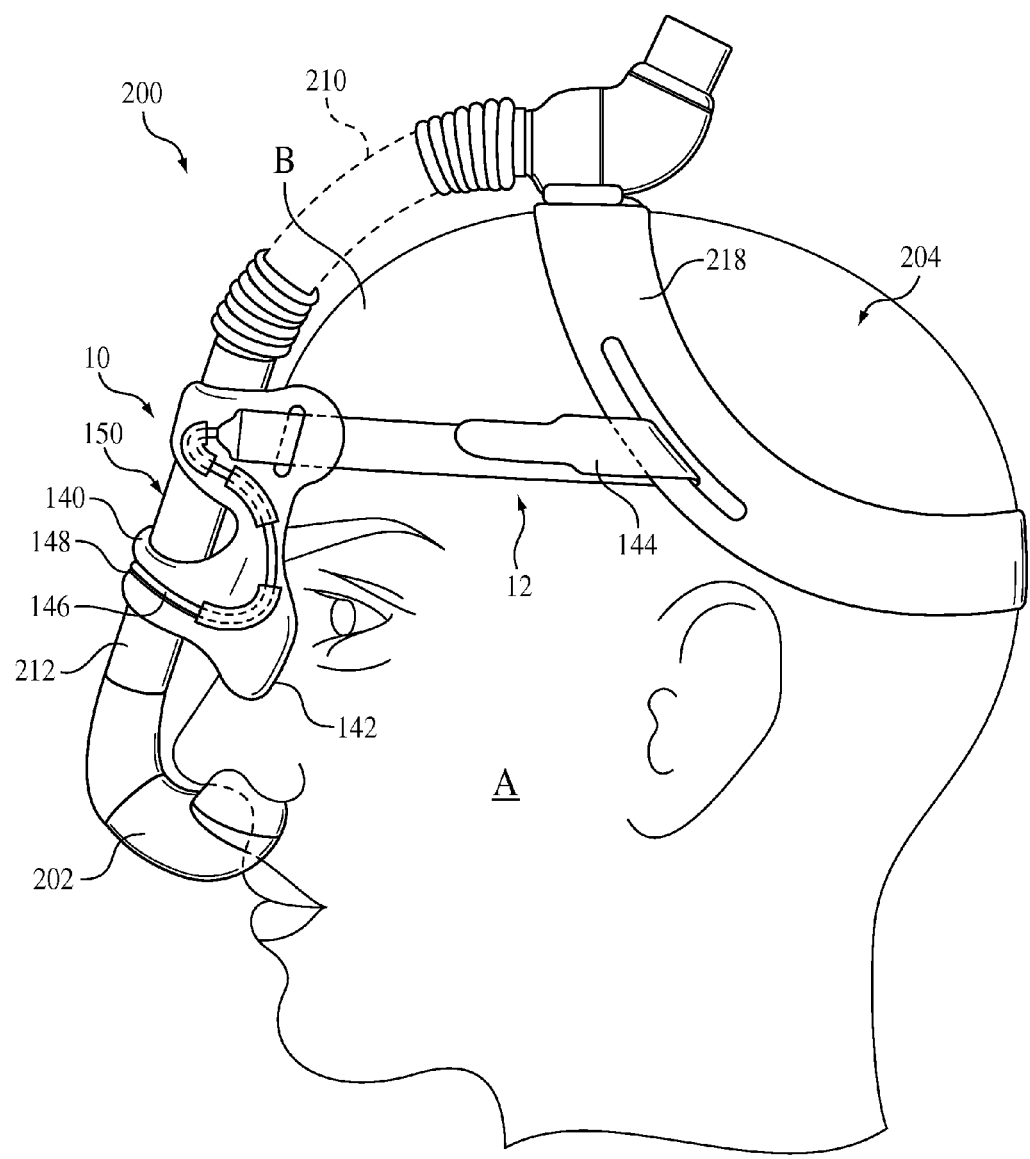
FIG. 26 is a side view of another embodiment of an adjustable conduit coupling assembly according to the principles of the present invention shown attached to a user via a headgear assembly.
Figure 27:
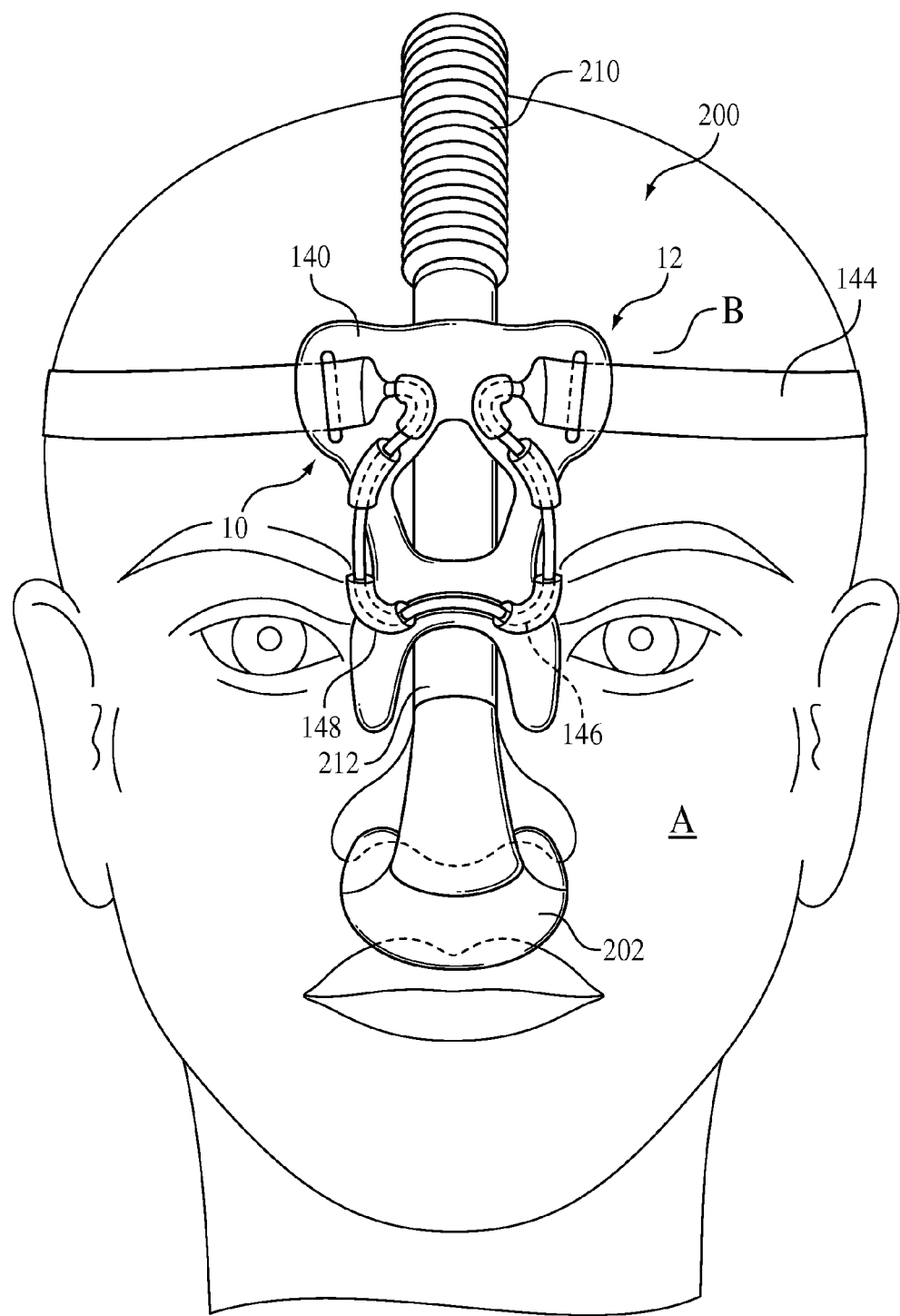
FIG. 27 is a front view of the adjustable conduit coupling assembly of FIG. 26 shown attached to a user via a headgear assembly.
Figure 28:
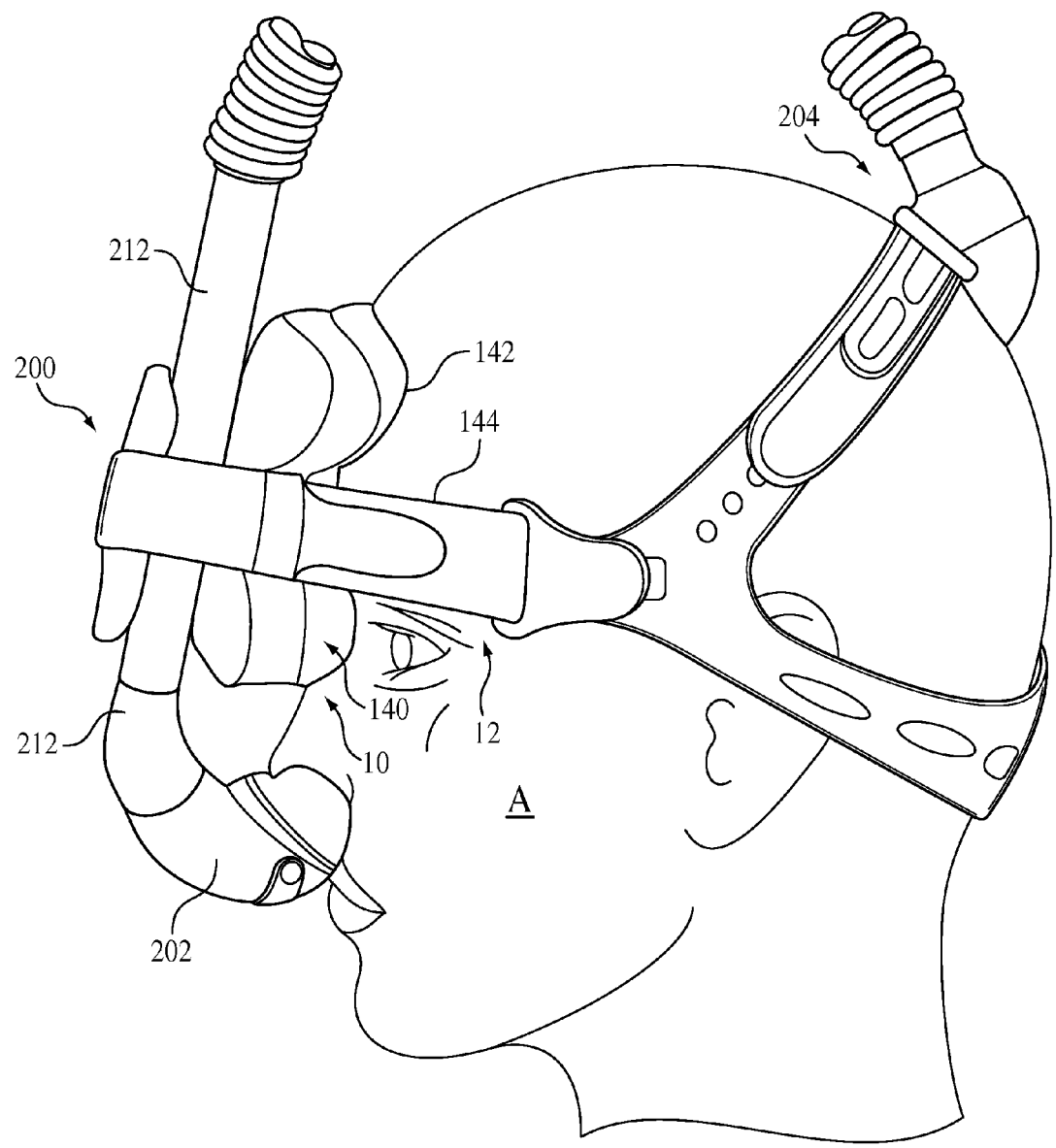
FIG. 28 is a side view of a further embodiment of an adjustable conduit coupling assembly according to the principles of the present invention.
Figure 29:
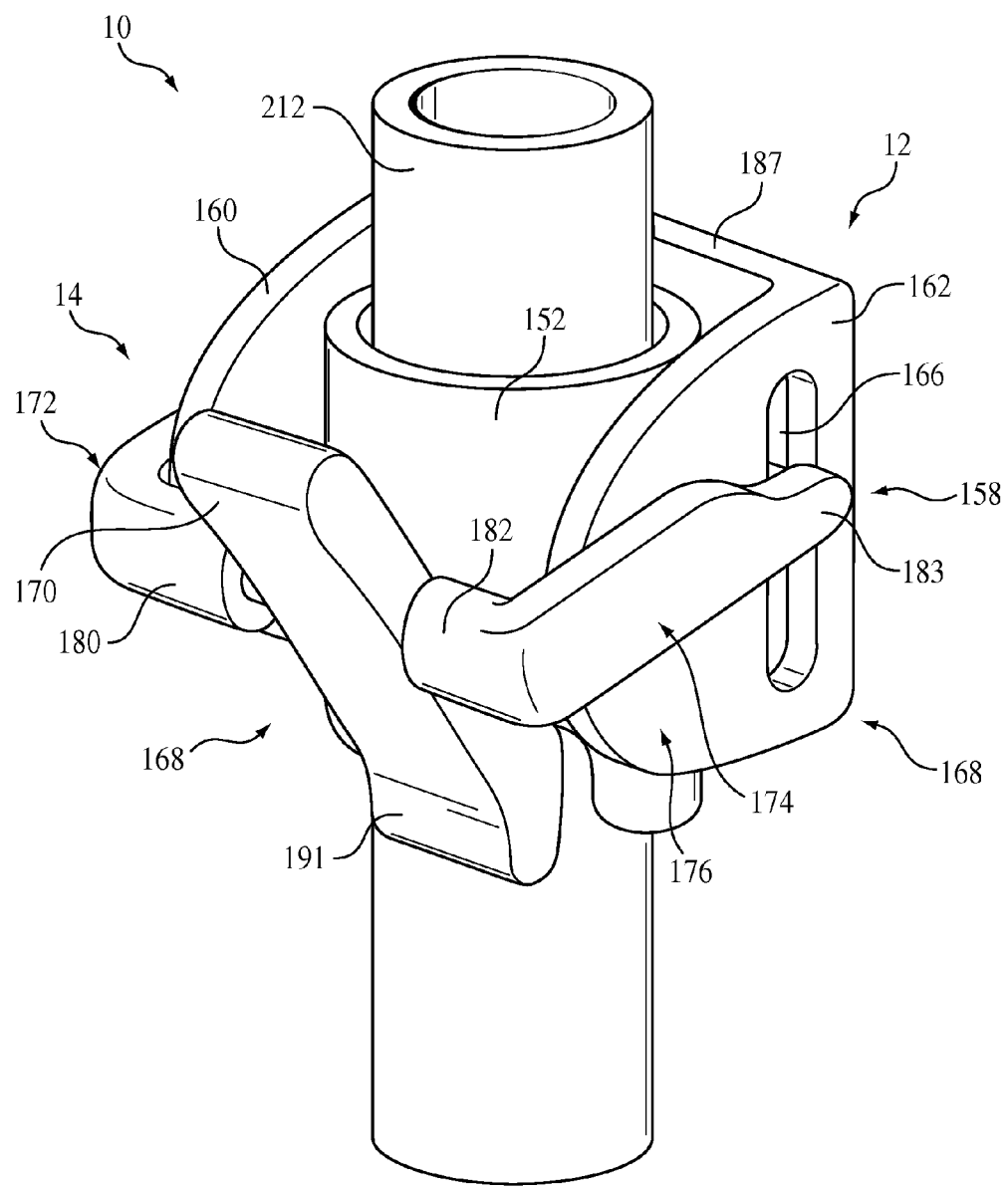
FIG. 29 is a perspective view of a still further embodiment of an adjustable conduit coupling assembly according the principles of the present invention.
Figure 30:
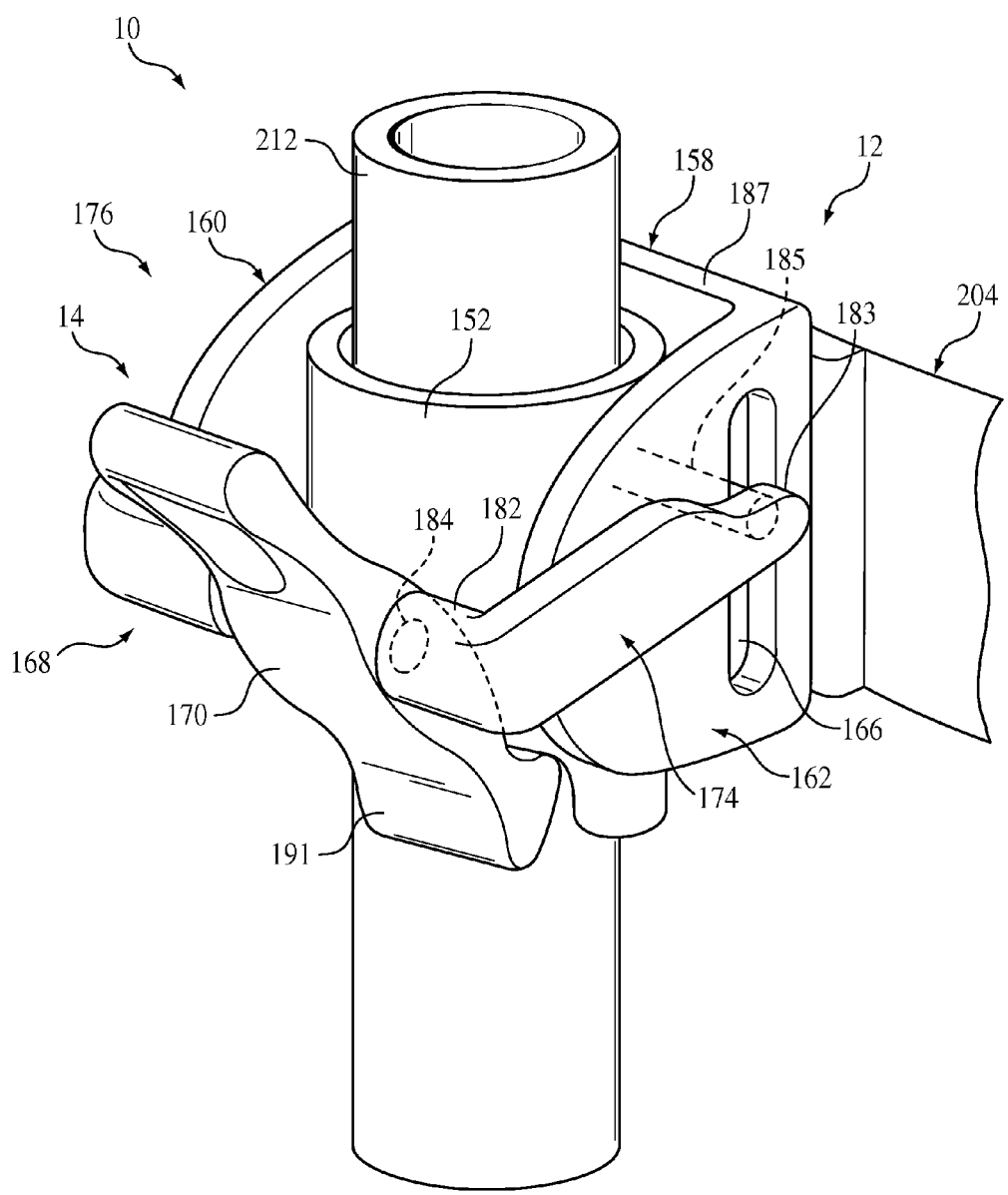
FIG. 30 is a further perspective view of the adjustable conduit coupling assembly of FIG. 29.

As best seen in FIGS. 26 and 27, in a further embodiment, a cord 146 is provided and attached to strap 144. This cord is positionable within a groove 148 that extends along contact member 140. In operation, tightening of strap 144 tightens cord 146 within groove 148. This provides distributed contact of the contour adjustment surface 142 against the user's face A.

In a further embodiment, coupling retention assembly 12 is directly or indirectly attached to headgear assembly 204. Importantly, coupling retention assembly 12 is used to hold conduit coupling 212 in a set position with respect to the user's face A, while headgear assembly 204 is used to attach the entire structure, including patient interface device 202 and conduit coupling assembly 10 against the user's face A. In addition, as discussed above, coupling retention assembly 12 may be removably attached to headgear assembly 204.

A still further embodiment of conduit coupling assembly 10 according to the principles of the present invention is illustrated in FIGS. 29-36. In this embodiment, adjustment assembly 14 includes a coupling collar 152 attached to or otherwise surrounding a portion of the conduit coupling 212. Coupling collar 152 includes a collar projection 154, which includes an elongate slot 156 extending through and along the collar projection. Further, coupling collar 152 is pivotally connected to a mounting bracket 158. Mounting bracket 158 is attachable to headgear assembly 204, as discussed above, and is utilized as coupling retention assembly 12 in conduit coupling assembly 10.

Mounting bracket 158 includes a first arm 160 and a second, opposing arm 162. First arm 160 includes a first elongate slot 164 extending through and along the first arm 160. A second elongate slot 166 is defined in second arm 162 such that the second slot extends through and along the second arm.

Figure 31:
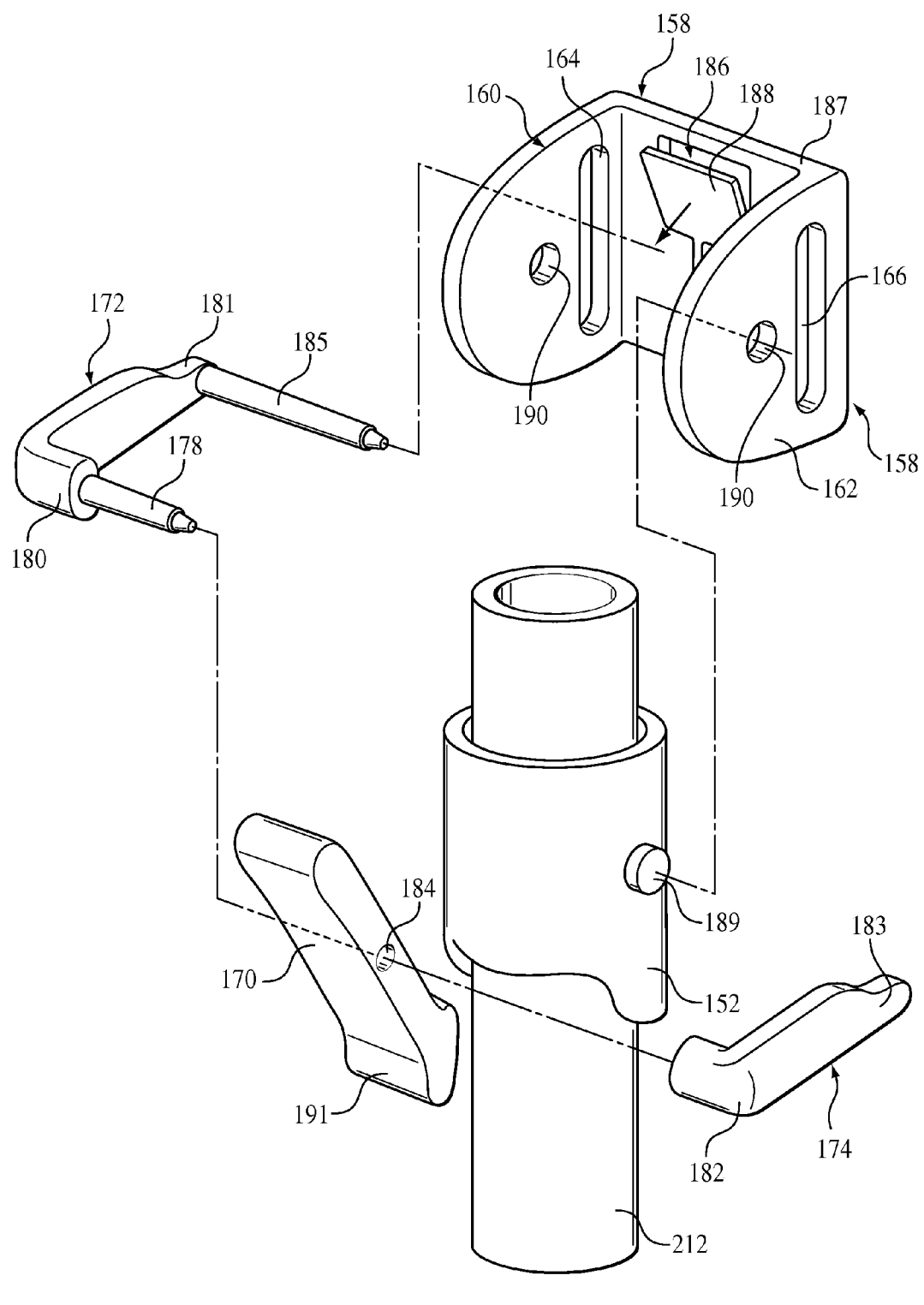
FIG. 31 is an exploded view of the adjustable conduit coupling assembly of FIG. 29.

In order to allow adjustability of conduit coupling assembly 10 in this embodiment, a pivot mechanism 168 including a locking lever 170 is attached between a first arm 172 and second, opposing arm 174 of a pivot bracket 176. In particular, and as best seen in FIG. 31, first arm 172 includes a first end 180 and a second end 181, and second arm 174 of pivot bracket 176 includes a first end 182 and a second end 183. In order to effect a pivoting arrangement of locking lever 170, a pivot pin 178 is attached to first end 180 of first arm 172 and extends through a lever orifice 184 on locking lever 170, and is further attached to first end 182 of second arm 174. Such an arrangement allows the lever 170 to pivot between the open position and a locked position.

In order to allow entire conduit coupling assembly 10 to pivot, a position bar 185 is attached between second end 181 of first arm 172 and second end 183 of second arm 174. In particular, position bar 185 extends through first slot 164 of first arm 160 of mounting bracket 158, further through slot 156 of coupling collar 152, and through second slot 166 of second arm 162 of mounting bracket 158. Due to the elongated shape of slots 156, 164, 166, position bar 185 is allowed to freely move and allow positioning and orientation of coupling collar 152, and thus conduit coupling 212. In addition, the size and shape of slots 156, 164, 166 define the limits of movement and allow secured, yet free, positioning and orientation of conduit coupling 212.

In order to counteract the force applied by the locking lever 170 when in the locked position, an urging structure 186 is attached to a base portion 187 of mounting bracket 158. In particular, urging structure 186 urges an inner portion of coupling collar 152, and therefore conduit coupling 212, is urged away from base portion 187 of mounting bracket 158. In operation, locking lever 170 is operable to an open position, such that coupling collar 152 is movable, and a locked position, such that the coupling collar is held in a specified position and orientation by the force of locking lever 170 and the opposing force of urging structure 186. The coaction of locking lever 170 and urging structure 186 serves to simultaneously lock both coupling collar 152 and conduit coupling 212 extending therethrough.

Figure 32:
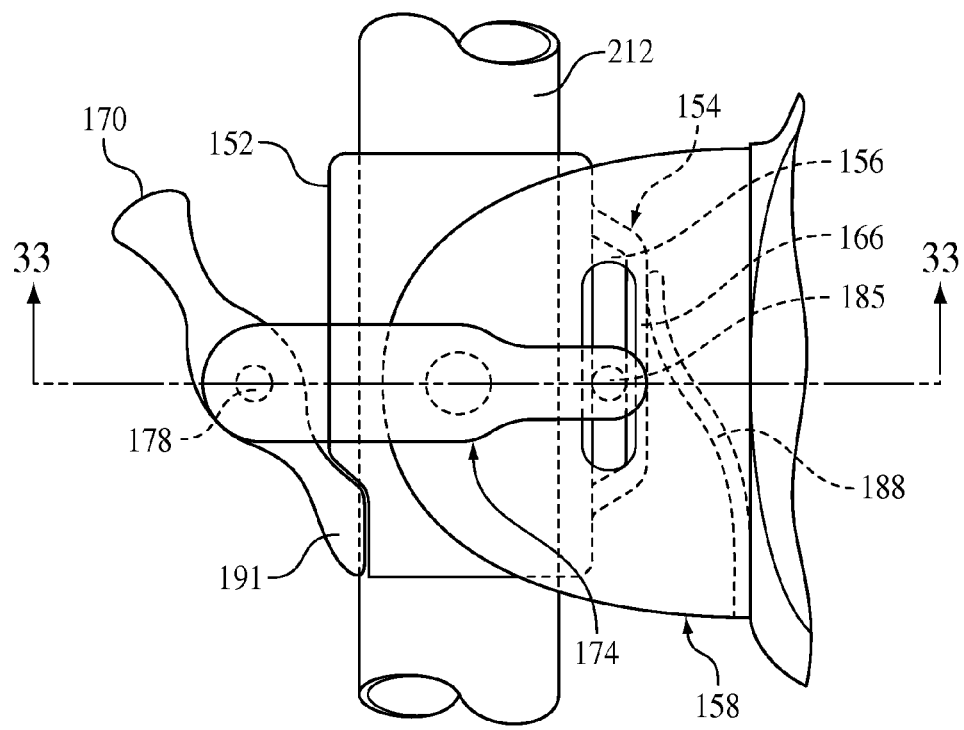
FIG. 32 is a side and partial sectional view of the adjustable conduit coupling assembly of FIG. 29.
Figure 33:
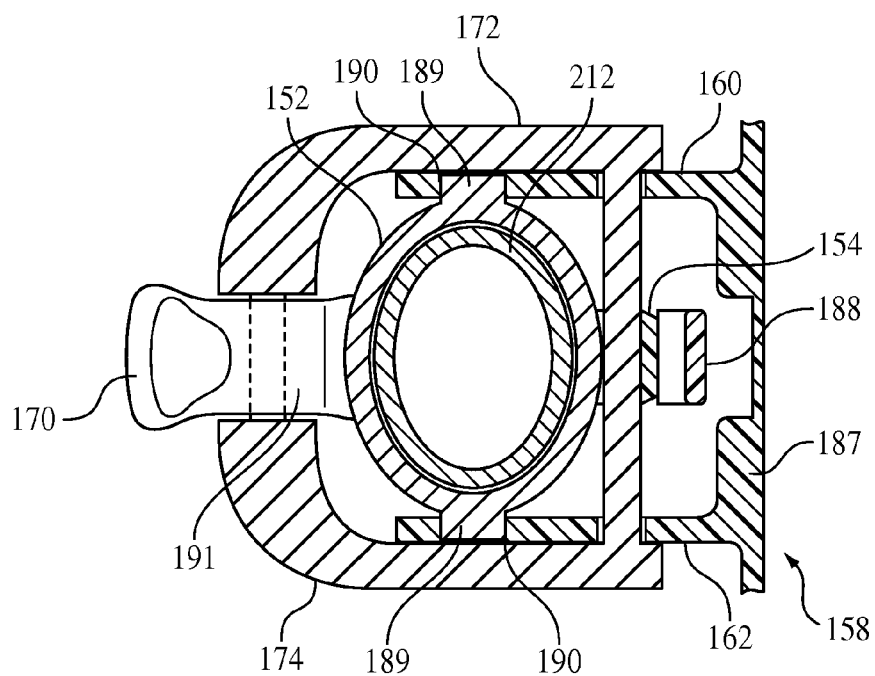
FIG. 33 is a sectional view along lines 33-33 of the adjustable conduit coupling assembly of FIG. 32.

As best seen in FIGS. 31-33, urging structure 186 may be a spring tab 188, which contacts the collar projection 154 and urges it away from base portion 187 of mounting bracket 158. In this embodiment, coupling collar 152 is pivotally attached through the use of a pair of opposed pivot buttons 189 extending from coupling collar 152. These pivot buttons are sized and shaped so as to mate within pivot orifices 190 extending through first arm 160 and second arm 162 of mounting bracket 158. Accordingly, urging structure 186, such as spring tab 188, urges collar projection 154 at a point that urges an upper portion of coupling collar 152 away from the user's forehead B, and coupling collar 152 (and thus conduit coupling 212) pivots about the pivot buttons 189 and pivot orifices 190.

Figure 34:
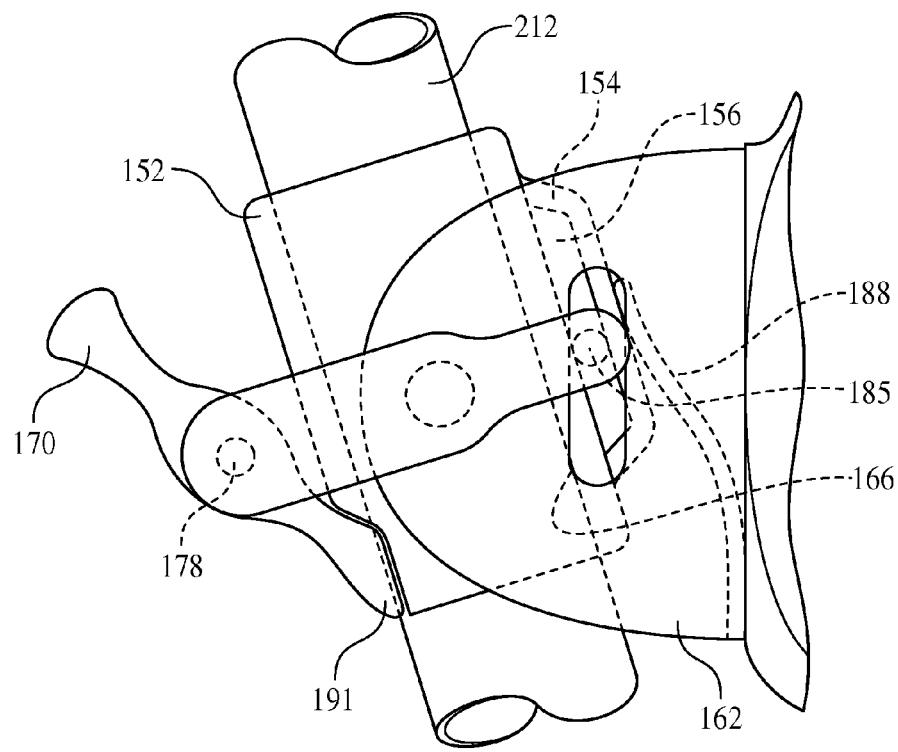
FIG. 34 is a side and partial sectional view of the adjustable conduit coupling assembly of FIG. 29 in a first tilt position.
Figure 35:
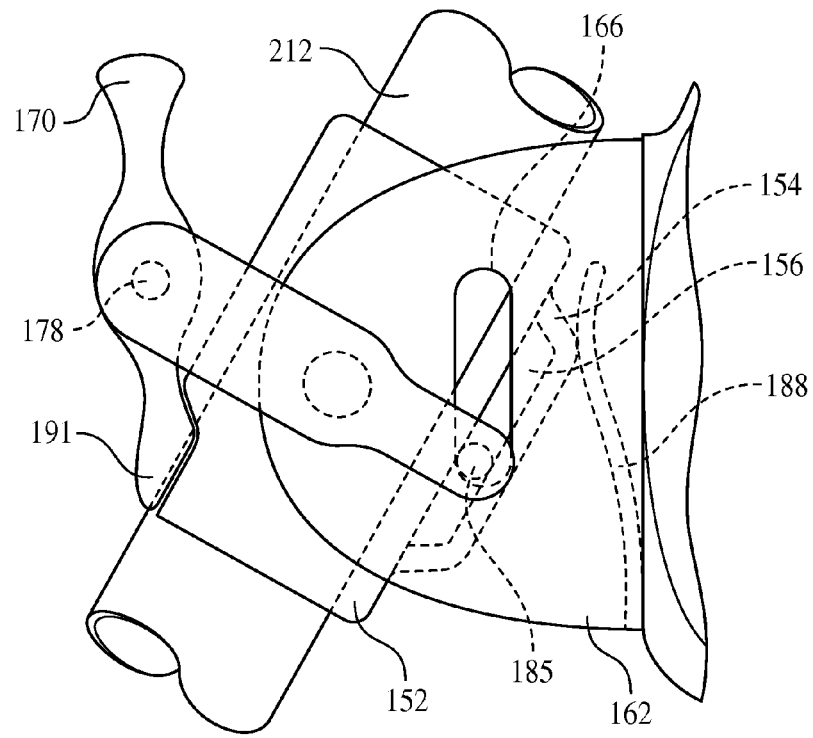
FIG. 35 is a side and partial sectional view of the adjustable conduit coupling assembly of FIG. 29 in a second tilt position.

As seen in FIGS. 34 and 35, the coupling collar is shown in various lockable positions, which utilized the forces of urging structure 186 and locking lever 170 to hold the collar 152 in place. In use, locking lever 170 is pivoted out of contact with coupling collar 152 and/or conduit coupling 212, and position bar 185 is moved along slots 156, 164, 166 until the desired position is reached. Once the desired position is reached, locking lever 170 is re-engaged and coupling collar 152 locked.

Figure 36:
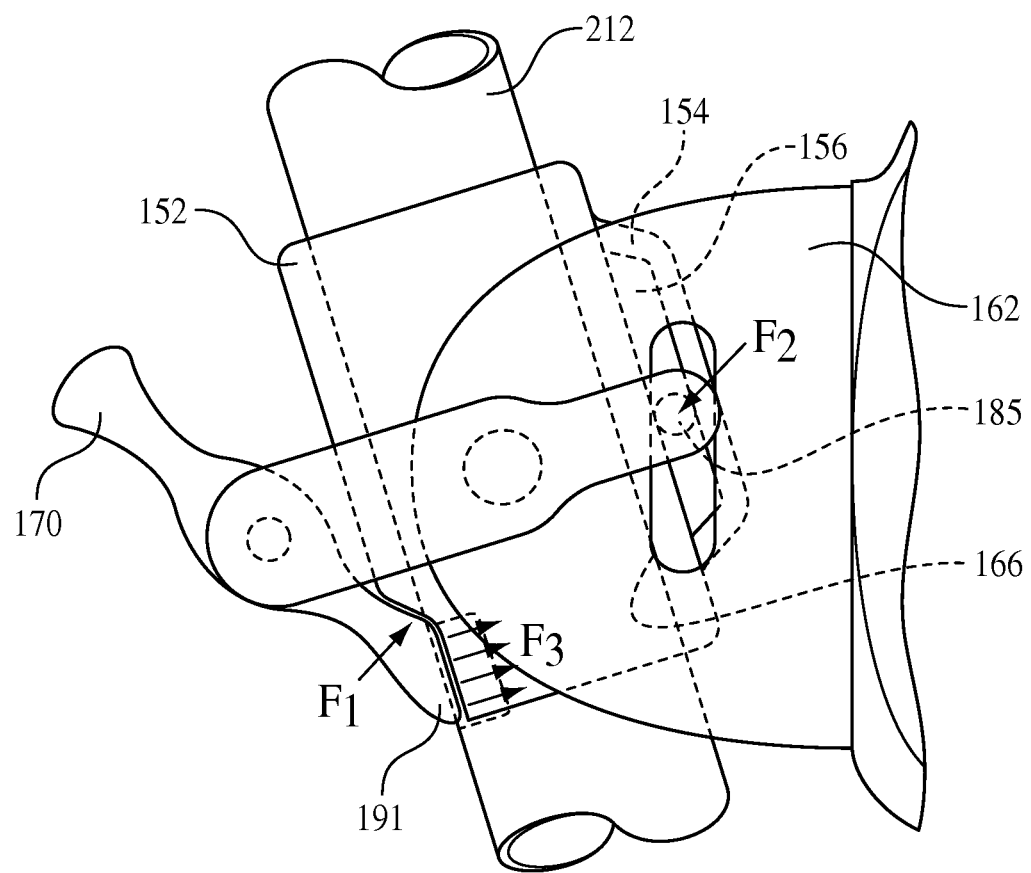
FIG. 36 is a side and partial sectional view of the adjustable conduit coupling assembly of FIG. 29 illustrating the force distributions.

FIG. 36 illustrates a force diagram illustrating the locking function of the present embodiment. In particular, position bar 185 is locked by two counteracting forces $F_1$ and $F_2$. $F_1$ acts on the outer surface of coupling collar 152 and/or conduit coupling 212, which pulls pivot bracket 176 forward, which generates the force $F_2$ from position bar 185. In this manner, the application of forces $F_1$ and $F_2$, together with the biasing and urging force from urging structure 186, serves to clamp coupling collar 152 in the desired location and position, and this location and position is not predetermined, instead set by the user.

As discussed above, in this embodiment, locking lever 170 may contact coupling collar 152 and/or conduit coupling 212. In addition, the profile of a contact end 191 of locking lever 170 may be substantially similar or identical to the profile of coupling collar 152 and/or conduit coupling 212. Again, as seen in the force diagram of FIG. 36, this matched profiling and/or contour would provide enhanced contact force, and will also generate force $F_3$. Force $F_3$ is used in laterally locking conduit coupling 212 within coupling collar 152 by clamping conduit coupling 212 against an inside surface (acting as the counter force) of coupling collar 152. Accordingly, the conduit coupling 212 is laterally adjustable within coupling collar 152 when locking lever 170 is in an open position, and is prevented from lateral movement when locking lever 170 is in a locked position and contacting end 191 of locking lever 170 against coupling collar 152 and/or conduit coupling 212.

In order to prevent rotation of conduit coupling 212 within coupling collar 152, it is envisioned that conduit coupling 212 and/or coupling collar 152 will have a non-circular profile, such that such rotation cannot occur. For example, in one exemplary embodiment, and as best illustrated in FIGS. 29-31 and 33, conduit coupling 212 and coupling collar 152 may have an elliptical profile, which would not detrimentally affect the flow of gas through conduit coupling 212, but would prevent rotation of conduit coupling 212 within coupling collar 152. As discussed above, urging structure 186 may be a spring tab 188, but any such urging mechanism or structure is envisioned, such as a coil spring or the like.

Figure 37:
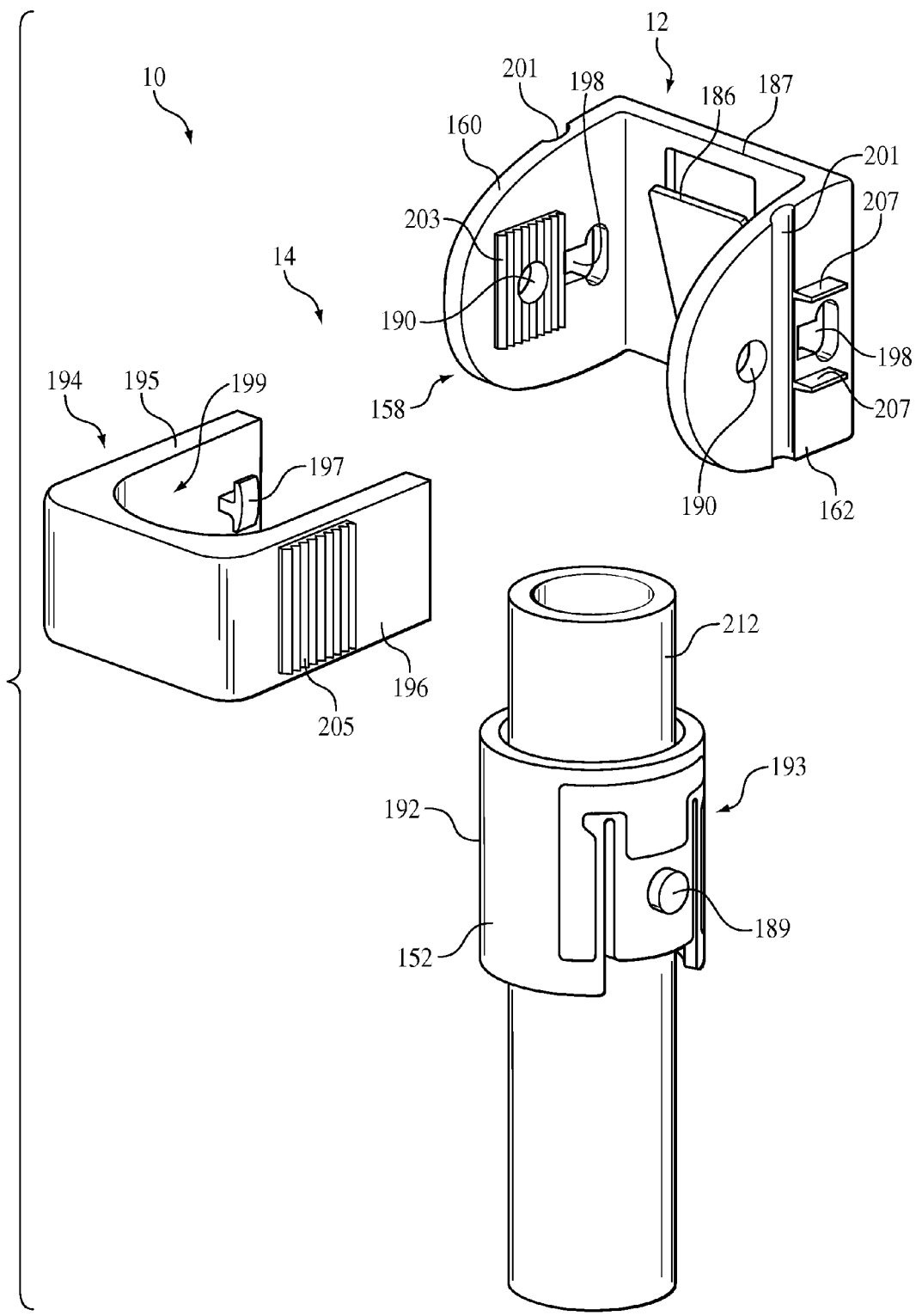
FIG. 37 is an exploded view of a further embodiment of an adjustable conduit coupling assembly according the principles of the present invention.

Yet another embodiment of the adjustable conduit coupling assembly 10 is illustrated in FIGS. 37-38B. In this embodiment, and as discussed above in the previous embodiment, conduit coupling assembly 10 includes a coupling collar 152 attached to a portion of conduit coupling 212. However, in this embodiment, coupling collar 152 includes a first spring tab 192 and a second, opposing spring tab 193 (not shown). Each of first spring tab 192 and second spring tab 193 includes a pivot button 189, which, as discussed above, are sized and shaped so as to at least partially mate with or extend through a respective pivot orifice 190 on mounting bracket 158. Accordingly, coupling collar 152 is pivotable about pivot buttons 189 on spring tabs 192, 193. Further, the squeezing forces of spring tabs 192, 193 serve to lock conduit coupling 212 in place, thereby preventing lateral movement.

In this embodiment, a U-shaped clamping bracket 194 having a first arm 195 and a second arm 196 is used to lock and unlock the mechanism. In particular, each arm 195, 196, and, in particular, an inner surface of each arm 195, 196, includes a locking projection 197 extending therefrom and configured and sized to mate with a locking orifice 198 extending through each arm 195, 196 of mounting bracket 158.

As discussed above in connection with the previous embodiment, an urging structure 186, such as spring tab, is provided to urge the inner portion of coupling collar 152 away from base portion 187 of mounting bracket 158. In addition, in order to effect this clamping motion of clamping bracket 194, an inner surface 199 of clamping bracket 194 can be beveled, such that the clamping bracket is positionable over arms 160, 162 of mounting bracket 158 and movable to an open position, where the coupling collar 152 is movable, and into a locked position. In the locked position, coupling collar 152 is held in a specified position and orientation by the pressure of the beveled inner surface 199 of clamping bracket 194 against the arms of mounting bracket 158, which are thereby urged against spring tabs 192, 193 of the coupling collar 152.

As best seen in FIGS. 38A and 38B, in order to attain the open position, clamping bracket 194 is slid forward, and arms 160, 162 of mounting bracket 158 are not deflected or urged inward, and coupling collar 152, and, therefore, conduit coupling 212, are adjustable about pivot buttons 189. When clamping bracket 194 is moved inward toward base portion 187 of mounting bracket 158, arms 160, 162 are deflected and urged inwardly into the locked position and thereby prevent coupling collar 152 from further movement, whether pivotally or laterally.

In order to provide better deflection characteristics to arms 160, 162, an elongate notch 201 extends partially through and along each arm. Elongate notch 201 provides better flexibility, much like a living hinge, to each arm 160, 162 when clamping bracket 194 is moved to the locked position. In essence, elongate notch 201 provides a flex point on each arm 160, 162, and, therefore, prevents the possibility of cracking, breaking or otherwise damaging the arms during repeated use. In addition, notch 201 allows arms 160, 162 to deform in use, as shown for example in FIG. 38A, thereby providing a stronger "grip" on coupling collar 152 and conduit coupling 212.

In order to provide better gripping characteristics when clamping bracket 194 is moved to a locked position, a gripping surface 203 can be displaced or positioned on at least a portion of an inner surface of arms 160, 162 of mounting bracket 158. In operation, gripping surface 203 contacts spring tabs 192, 193 and provides a frictional lock to hold the coupling collar 152 in the desired position.

It is also envisioned that clamping bracket 194 includes a contact gripping surface 205 on a portion of an outer surface of clamping bracket 194. Gripping surface 205 assists the user in gripping and manipulating clamping bracket 194 between the open position and the locked position. Also, as discussed above in connection with the previous embodiment, the present embodiment may also use a conduit coupling 212 and/or coupling collar 152 with a non-circular profile to prevent rotation of the conduit coupling within the coupling collar. In addition, urging structure 186 may be a coil spring or the like. In order to more easily allow set movement of clamping bracket 194, alignment tabs 207 can be provided on either side of locking orifices 198 and extend from arms 160, 162 of mounting bracket 158. Such tabs 207 allow the user to more easily move the clamping bracket 194 from the open position to the locked position along the locking orifices 198.

In this manner, the present invention provides a conduit coupling assembly 10 that provides full adjustability of conduit coupling 212. Further, conduit coupling assembly 10 of the present invention provides flexibility of adjustment, orientation and position of conduit coupling 212 with respect to the user's face A and/or the user's forehead B. Still further, the present invention provides a conduit coupling assembly 10 that allows for the adjustment of conduit coupling 212 without jeopardizing the seal between the patient interface device and the user's face A. Accordingly, conduit coupling assembly 10 of the present invention provides a continuously adjustable and retainable conduit coupling 212.

FIG. 39 illustrates still another embodiment of a conduit coupling assembly 10 according to the principles of the present invention. This embodiment of the conduit coupling assembly is generally similar to that shown and described above with respect FIGS. 17-19. One difference between these two embodiments resides in the configuration of collar 240 and tilt arm 242. Collar 240 and tilt arm 242 are generally similar to collar 16 and tilt arm 100 shown in FIGS. 17-19, except that the exterior surface of collar 240 includes at least one flat portion 244. Likewise, tilt arm 242 includes an orifice 246 having a curved surface and a flat surface portion 248 that abuts flat portion 244 of collar 240 when the conduit coupling assembly is assembled. Although one flat surface on the collar and one corresponding flat surface on the interior of orifice 246 are contemplated by the present invention, more than one flat surfaces can be provided. For example, FIG. 39 illustrates two flat surfaces 244 and 250 on collar 240 and two flat surfaces 248 and 252 on tilt arm 242.

The purpose of the flat surfaces is to control the movement of the conduit coupling (not shown) relative to the rest of the headgear by controlling the movement of collar 140 within tilt arm 242. More specifically, the rounded or curved surfaces of the collar and tilt arm permit rotational movement as indicated by arrows 254 so that the patient interface can be moved toward and away from the patient and locked into place when a desired position is reached. However, the flat surfaces of the collar and tilt arm restrict rotational movement as indicated by arrows 256, so that the patient interface does not twist or rotate on the user's head. The flat surfaces arranged in this configuration also restrict lateral movement, i.e., side-to-side movement, of the patient interface across the user's face.

FIG. 40 illustrates a further alternative configuration for a collar 260 suitable for use in the conduit coupling assembly of the present invention, which is similar to that of FIGS. 17-19 and 39. This configuration is provided to show an alternative location for flat surfaces 262 and 264 provided on the collar. Corresponding flat surfaces would be provided in the interior surface of the orifice of the tilt arm. In this configuration, the flat surfaces restrict movement of the patient interface toward and away from the face as well as restrict rotational movement indicated by arrow 256. However, the remaining curved surfaces permit lateral movement of the patient interface across the user's face. It should be understood that the present invention contemplates that the features of the is embodiment can be combined with that of other embodiments so that additional positional control of the patient interface can be provided by other adjustable elements.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An adjustable conduit coupling assembly comprising:
   (a) an adjustment assembly operatively coupled to a conduit coupling and configured to permit adjustment of a position of the conduit coupling with respect to a user's face; and
   (b) a coupling retention assembly configured to retain the adjustment assembly in a predetermined position with respect to the user's face, and wherein the conduit coupling is adjustable from a first position to a second position by the adjustment assembly and retainable in the second position by the adjustment assembly over a range of positions, wherein the adjustment assembly comprises:
      a tilt assembly configured to adjustably tilt the conduit coupling with respect to a user's face such that the conduit coupling rotates in a plane that is parallel with a centerline of the user's face; or
      an extension assembly configured to adjustably position the conduit coupling such that the conduit coupling is movable in a direction that is generally parallel to the centerline of the user's face; or
      both the tilt assembly and the extension assembly, and wherein the adjustment assembly comprises:
         a coupling collar attached to a portion of the conduit coupling and providing clamping surfaces on opposing sides of the coupling collar; and
         a clamping mechanism having at least two clamp arms and a locking mechanism, each clamp arm configured to contact a respective and opposing clamping surface, wherein the clamping mechanism is operable between an open position, in which the coupling collar is adjustable with respect to the user's face, and a clamped position, in which the coupling collar is held in the second position, wherein the locking mechanism is configured to retain the clamp arms in the clamped position and to release the clamp arms in the open position, and wherein at least one of the clamp arms is movable toward and away from the other of the clamp arms and into and out of contact with the respective and opposing clamping surface in a direction perpendicular to a longitudinal axis of the conduit coupling by operation of the locking mechanism.

2. The adjustable conduit coupling assembly of claim 1, wherein the clamping surfaces are planar surfaces parallel to the longitudinal axis of the conduit coupling.

3. The adjustable conduit coupling assembly of claim 1, wherein the locking mechanism comprises:
   a screw element,
   a thumb screw,
   a ratchet mechanism,
   a latch mechanism,
   means for retaining the clamp arms in the clamped position,
   a slide track configured to permit at least one of the clamp arms to slide along the slide track between the open position and the clamped position, wherein the at least one clamp arm further comprises a track engagement member configured to slidingly engage with the slide track,
   a pair of levers in operational communication with at least one of the clamp arms operable to urge the clamp arms to the clamped position and release the clamp arms to the open position
   or any combination thereof.

4. The adjustable conduit coupling assembly of claim 1, further comprising a coupling collar retainer member attached to the coupling collar and configured to retain the coupling collar when the clamp arms are in the open position.

5. The adjustable conduit coupling assembly of claim 4, wherein at least one surface of the coupling collar includes at least one projection set extending therefrom, the at least one projection set configured to slidingly engage a track positioned on a surface of at least one of the clamp arms, wherein, when the clamp arms are in the open position, the projection set is slidable along the track and positionable along the track in a specified set point to achieve a desired coupling collar position.

6. The adjustable conduit coupling assembly of claim 1, wherein the coupling retention assembly further comprises a retainer clip configured to attach to a headgear assembly.

7. An adjustable conduit coupling assembly comprising:
(a) an adjustment assembly operatively coupled to a conduit coupling and configured to permit adjustment of a position of the conduit coupling with respect to a user's face; and
(b) a coupling retention assembly configured to retain the adjustment assembly in a predetermined position with respect to the user's face, wherein the coupling retention assembly further comprises at least one arm and wherein the adjustment assembly further comprises a coupling collar attached to the conduit coupling and engageable with the at least one arm and a flexible latch arm extending from a top surface of the coupling collar, the latch arm having a latch projection extending therefrom, wherein the conduit coupling is adjustable from a first position to a second position by the adjustment assembly and retainable in the second position by the adjustment assembly over a range of positions, wherein the adjustment assembly comprises:
a tilt assembly configured to adjustably tilt the conduit coupling with respect to the user's face such that the conduit coupling rotates in a plane that is parallel with a centerline of the user's face, wherein the at least one arm further comprises a plurality of track slots positioned along a surface of the arm and a plurality of latch slots position along the surface of the arm above the plurality of track slots, the coupling collar further comprising a track projection extending from a surface of the coupling collar and configured to slidingly engage at least one of the plurality of track slots of the arm, the latch projection being configured to slidingly engage at least one of the plurality of latch slots, wherein each of the plurality of track slots of the arm extend at a predetermined angle along the surface of the arm in a manner wherein the plurality of track slots are arranged in an arcuate fashion along the surface of the arm, and wherein each of the latch slots extending at a predetermined angle along the surface of the arm in a manner wherein the plurality of latch slots are arranged in an arcuate fashion along the surface of the arm thereby providing the tilt assembly as a plurality of selectable and latchable tilt positions of the coupling collar and the conduit coupling relative to the conduit coupling in the plane.

8. The adjustable conduit coupling assembly of claim 7, further comprising an extension assembly configured to adjustably position the conduit coupling such that the conduit coupling is movable in a direction that is generally parallel to the centerline of the user's face, wherein the extension assembly comprises an extension collar surrounding and slidably engaged with the conduit coupling, wherein the extension collar is engageable with the conduit coupling to prevent sliding thereof, and disengageable with the conduit coupling to allow sliding thereof, and thereby providing adjustable positioning of the conduit coupling.

9. An adjustable conduit coupling assembly comprising:
(a) an adjustment assembly operatively coupled to a conduit coupling and configured to permit adjustment of a position of the conduit coupling with respect to a user's face; and
(b) a coupling retention assembly configured to retain the adjustment assembly in a predetermined position with respect to the user's face, wherein the coupling retention assembly further comprises at least one tilt arm and wherein the adjustment assembly further comprises a coupling collar attached the conduit coupling and engageable with the at least one tilt arm, wherein the conduit coupling is adjustable from a first position to a second position by the adjustment assembly and retainable in the second position by the adjustment assembly over a range of positions, wherein the adjustment assembly comprises:
a tilt assembly configured to adjustably tilt the conduit coupling with respect to the user's face such that the conduit coupling rotates in a plane that is parallel with a centerline of the user's face, wherein the at least one tilt arm has a tilt arm orifice having a first rounded surface defined therein, and wherein a second rounded surface is operatively provided on the conduit coupling, wherein the second rounded surface is positionable within the tilt arm orifice in engagement with the first rounded surface and slidable along the conduit coupling, wherein the tilt arm orifice is adjustable around the coupling collar in a clamped position and an open position.

10. The adjustable conduit coupling assembly of claim 9, further comprising an extension assembly configured to adjustably position the conduit coupling such that the conduit coupling is movable in a direction that is generally parallel to the centerline of the user's face, wherein the extension assembly further comprises an extension collar engageable and disengageable with the conduit coupling, such that the conduit coupling is slidingly adjustable in a lateral position.

11. An adjustable conduit coupling assembly comprising:
(a) an adjustment assembly operatively coupled to a conduit coupling and configured to permit adjustment of a position of the conduit coupling with respect to a user's face; and
(b) a coupling retention assembly configured to retain the adjustment assembly in a predetermined position with respect to the user's face, wherein the coupling retention assembly further comprises at least one tilt arm and wherein the adjustment assembly further comprises a coupling collar attached the conduit coupling and engageable with the at least one tilt arm, wherein the conduit coupling is adjustable from a first position to a second position by the adjustment assembly and retainable in the second position by the adjustment assembly over a range of positions, wherein the adjustment assembly comprises:
a tilt assembly configured to adjustably tilt the conduit coupling with respect to the user's face such that the conduit coupling rotates in a plane that is parallel with a centerline of the user's face, wherein the tilt assembly comprises a first adjustable pivot member structured to be selectively expanded and contracted over a first distance to at least contact and push a first portion of the conduit coupling and a second adjustable pivot member positioned above the first adjustable pivot member and structured to be selectively expanded and contracted over a second distance parallel to the first distance to at least contact and push a second portion of the conduit coupling separate from and positioned above the first portion of the conduit coupling, wherein when one of the first adjustable pivot member and the second adjustable pivot member is expanded, the other of the first adjustable pivot member and the second adjustable pivot member is contracted, thereby providing an adjustable tilt assembly.

12. The adjustable conduit coupling assembly of claim 11, wherein the adjustable pivot members comprise:

a piston operable to extend and retract through insertion and removal of a material to and from a piston chamber;

a bladder operable to extend and retract through insertion and removal of the material to and from a bladder chamber; or a combination of the piston and the bladder.

13. An adjustable conduit coupling assembly comprising:
a conduit coupling; and
an adjustment assembly operatively coupled to the conduit coupling and configured to permit adjustment of a position of the conduit coupling with respect to a user's face, wherein the adjustment assembly includes a contact member coupled to the conduit coupling and having a contoured adjustment surface configured to contact a user's face, wherein movement and contact of the contoured adjustment surface adjusts the position of the conduit coupling relative to the user, the contact member having a top portion, a bottom portion, and a cutout portion provided in between the top portion and the bottom portion, the top portion having a first opening and the bottom portion having a second opening, wherein the conduit coupling is inserted through the bottom opening and the top opening and is movable up and down within the contact member.

14. The adjustable conduit coupling assembly of claim 13, further comprising at least one strap attachable between the contact member and a headgear assembly configured to retain a mask coupled to the conduit coupling in a sealed position on the user's face.

15. The adjustable conduit coupling assembly of claim 14, further comprising:
a cord attached to the at least one strap; and
a groove extending along at least a portion of the contact member, wherein the cord is disposed in the groove, and wherein tightening of the at least one strap tightens the cord within the groove, thereby providing distributed contact of the contoured adjustment surface against the user's face.

16. A patient interface system, comprising:
(a) a mask shell and at least one mask port defined in the mask shell;
(b) a cushion operatively coupled to the mask shell;
(c) a conduit coupling in fluid communication with the mask port; and
(d) a conduit coupling assembly operatively coupled to the conduit coupling, the conduit coupling assembly including:
(i) a coupling retention assembly configured to retain the conduit coupling in a predetermined position with respect to the user's face; and
(ii) an adjustment assembly operatively coupled to the conduit coupling and configured to permit adjustment of the position of the conduit coupling, and wherein the conduit coupling is adjustable from a first position to a second position by the adjustment assembly and retainable in the second position by the adjustment assembly over a continuous range of positions, wherein the adjustment assembly comprises:
(1) a tilt assembly configured to adjustably tilt the conduit coupling with respect to a user's face such that the conduit coupling rotates in a plane that is parallel with a centerline of the user's face; or
(2) an extension assembly configured to adjustably position the conduit coupling such that the conduit coupling is movable in a direction that is generally parallel to the centerline of the user's face; or
(3) both the tilt assembly and the extension assembly, and wherein the adjustment assembly comprises:
a coupling collar attached to a portion of the conduit coupling and providing clamping surfaces on opposing sides of the coupling collar; and
a clamping mechanism having at least two clamp arms and a locking mechanism, each clamp arm configured to contact a respective and opposing clamping surface, wherein the clamping mechanism is operable between an open position, in which the coupling collar is adjustable with respect to the user's face, and a clamped position, in which the coupling collar is held in the second position, wherein the locking mechanism is configured to retain the clamp arms in the clamped position and to release the clamp arms in the open position, and wherein at least one of the clamp arms is movable toward and away from the other of the clamp arms and into and out of contact with the respective and opposing clamping surface in a direction perpendicular to a longitudinal axis of the conduit coupling by operation of the locking mechanism.

17. The system of claim 16, further comprising a headgear assembly operatively coupled to the coupling retention assembly.

18. The system of claim 17, wherein the coupling retention assembly further comprises a retainer clip configured to attach to the headgear assembly.

19. The system of claim 17, wherein the conduit coupling has a first end and a second end, wherein the first end of the conduit coupling is attached to the mask shell, and the second end of the conduit coupling is in fluid communication with a patient circuit, a conduit, a pressure support device, a gas source, or any combination thereof.

20. The system of claim 17, wherein the clamping surfaces are planar surfaces parallel to the longitudinal axis of the conduit coupling.

21. The system of claim 17, wherein the adjustment assembly further comprises a contact member affixed to the conduit coupling and having a contoured adjustment surface configured to contact a user's face, wherein movement and contact of the contoured adjustment surface adjusts the position of the conduit coupling relative to the user.

* * * * *